United States Patent [19]
Crabtree et al.

[11] Patent Number: 5,837,840
[45] Date of Patent: Nov. 17, 1998

[54] NF-AT POLYPEPTIDES AND POLYNUCLEOTIDES

[75] Inventors: Gerald R. Crabtree, Woodside; Jeffrey P. Northrop, Campbell, both of Calif.

[73] Assignee: Board of Trustees of Leland Stanford Jr. University, Stanford, Calif.

[21] Appl. No.: 124,981

[22] Filed: Sep. 20, 1993

[51] Int. Cl.$^6$ .................................................. C07H 21/04
[52] U.S. Cl. ..................... 536/23.4; 536/23.1; 536/24.3
[58] Field of Search .......................... 530/350; 435/69.1, 435/320.1, 240.2; 536/23.1, 23.5

[56] References Cited

FOREIGN PATENT DOCUMENTS

WO 94/15964   7/1994   WIPO .

OTHER PUBLICATIONS

Clipstone and Crabtree, "Identification of calcineurin as a key signalling enzyme in T–lymphocyte activation," *Nature*, 357:695–697 (1992).
Emmel, et al., "Cyclosporin A Specifically Inhibits Function of Nuclear Proteins Involved in T Cell Activation," *Science*, 246:1617–1620 (1989).
Flanagan et al., "Nuclear association of a T–cell transcription factor blocked by FK–506 and cyclosporin A," *Nature*, 352:803–807 (1991).
McCaffrey et al., "NF–AT$_p$, a T Lymphocyte DNA–binding Protein That is a Target for Calcineurin and Immunosuppressive Drugs," *J. Biol. Chem.*, 268(5):3747–3752 (1993).
McCaffrey et al., "Isolation of the Cyclosporin–Sensitive T Cell Transcription Factor NFATp," *Science*, 262:750–754 (1993).
Northrop et al., "Characterization of the Nuclear and Cytoplasmic Components of the Lymphoid–specific Nuclear Factor of Activated T Cells (NF–AT) Complex," *J. Biol. Chem.*, 268(4):2917–2923 (1993).
Northrop, S.P. et al. *Nature* 369:497–502 (1994).

*Primary Examiner*—Robert A. Wax
*Assistant Examiner*—Daniel S. Mytelka
*Attorney, Agent, or Firm*—Matthew P. Vincent; Isabelle M. Clauss; Foley, Hoag & Eliot LLP

[57] ABSTRACT

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

9 Claims, 16 Drawing Sheets

N's INDICATE REGIONS OF SEQUENCE AMBIGUITY

```
                                                                           54
GAA TTC CGC AGG GCG CGG GCA CCG GGG CGC GGG CAG GGC CGC TCG GAG CCA CCG CGC
CTT AAG GCG TCC CGC GCC CGT GGC CCC GCG GTC CCC AGC CTC GGT GGC GCG
 E   F   R   R   A   R   G   A   P   G   R   A   G   Q   G   R   S   E   P   P   R   A
     N   I   P   Q   A   T   H   R   G   A   R   G   A   L   G   A   T   A   Q

108
AGG TCC TAG GGC CGC GGC GGG CCC CGC CAC GCG CGC ACA CGC CCC TCG ATG ACT
TCC AGG ATC CCG GCG CCG CCC GGG GTG CGC GCG TGT GCG GGG AGC TAC TGA
 R   S   *   G   R   G   G   P   R   H   A   R   T   R   P   S   M   T
 G   P   R   A   A   G   P   A   T   R   A   H   T   P   L   D   D   F
 V   L   G   P   R   A   P   R   A   H   T   P   L             INITIATOR METHIONINE

162
TTC CTC CGG GGC GCG GGG AGG GCT GTC TTC CCG GAG ACC
AAG GAG GCC CCG CGC TCC CGA CAG AAG GGC CTC TGG
 F   L   R   G   A   R   E   P   G   A   R   A   V   F   P   E   T   P
 S   S   G   G   A   R   G   G   L   S   R   R   D   P

216
CGA CCC CGG CAG CGC GGG GCC ACT TCT CCT GTG CCT CCG CCC GCT CCA
GCT GGG GCC GTC GCG CCC CGC CGG TGA AGA GGA CAC GGA GGC CGA GGT
 R   P   R   Q   R   G   A   T   S   P   V   P   P   P   A   P
 D   P   A   A   R   G   S   A   R   P   L   L   C   L   R   P   A   L   H   T
 T   P   A   A   R                                                 S
```

FIG. 1A

```
                                                              270
CTC CCC GCC GCC GCG ATG CCA AGC ACC AGC TTT CCA GTC CCT TCC AAG
GAG GGG CGG CGG CGC TAC TCG TGG AAA GGT CAG AGG TTC
 L   P   A   A   A   M   P   S   T   S   F   P   V   P   S   K
 S   P   R   R   R   Y   C   W   K   G   Q   R   F
                                 D   A   K   H   Q   S   P   F   Q   V
                                                              324
TTT CCA CTT GGC CCT GCG GTC TTC GGG AGA GGA GAA ACT TTG GGG CCC
AAA GGT GAA CCG GGA CGC CAG CCC TCT CCT CTT TGA AAC CCC GGG
 F   P   L   G   P   A   V   F   G   R   G   E   T   L   G   P
 K   G   E   P   G   R   Q   P   S   P   L   *   N   P   G
 F   H   W   P   A   L   R   S   G   R   E   R   N   F   G   A   R
                                                              378
GCG GCG CCG GCA CCA TGA AGT CAG CGG AGG AAG AAC ACT ATG GCT ATG
CGC CGC GGC CGT ACT TCA GTC GCC TCC TTC TTG TGA TAC CGA TAC
 A   A   P   A   P   *   S   Q   R   R   K   N   T   M   A   M
 R   R   P   H   H   E   V   S   A   E   E   H   Y   G   Y
                         M   K   S   Q   R   R   K   T   L   W   L   C
                                                              432
GNN CGC GCG CCG GCG GCA CCC CCC TGC CGC TCC CCA CGG CGC ACT CCA CCC TGC
CNN GCG CGC CGG CGC CGT
 R   A   R   P   A   A
 A   R   A   R   R
                                                                    FIG. 1B

CAT CCT CCA ACG TCA GCC CCG CCC TGC CGC TCC CCA CGG CGC ACT CCA CCC TGC
```

FIG. 1C

```
                                                               648
TCG AGA TAA CCT CGT GCT TGG GCC CGG ACC ACA ATA ACC AGT TTT TCC ACG
AGC TCT ATT GGA GCA CGA CCG TGG TGT TGT TAT TGG TCA AAA AGG TGC
 S   R   D   N   P   R   A   W   A   C   Y   P   V   F   F   H   D
 R   E   I   T   S   C   V   L   G   L   P   T   I   T   S   F   P   R
                 621                                                   702
ATG TGG AGG TGG AAG ACG TCC CTA GCT CCA AAC GGT CCC CCC TCC ACG GCC
TAC ACC TCC ACC TTC TGC AGG GAT CGA GGT TTG CCA GGG AGG TGC CGG
 M   W   R   W   K   T   S   L   A   P   N   G   P   P   S   T   A
 C   G   G   E   V   R   K   R   D   V   S   Q   L   P   G   P   L   H   G
                 675                                                   756
ACG CTG AGT CTG CCC AGC CTG GAG TAC AGA GAC CCC TCG TGC CTG AGC CCG
TGC GAC TCA GAC GGG TCG GAC CTC ATG TCT CTG GGG AGC ACG GAC TCG GGC
 T   L   S   L   P   S   L   E   Y   R   D   P   S   C   L   S   P
 R   A   E   S   A   Q   P   S   A   W   G   L   Q   R   P   L   V   P   E   P   A   R
                 729                                                   810
GCC AGC CTG TCC TCC CGG AGC AAC TCA TGC AAT ACG TTG AGT CTC TAC GAG TCC
CGG TCG GAC AGG AGG GCC TCG TTG AGT ACG TCA TGC AAC TCA GAG ATG CTC AGG
 A   S   L   S   S   R   S   N   S   C   N   T   L   S   L   Y   E   S
 P   A   Q   P   V   L   P   A   C   P   L   S   R   G   A   L   Q   R   G   P   L   L   R   V   Q
                 783

FIG. 1D
```

```
                                                  864
AAC TAC TCG TAC CCG TAC GCG TCC CCC CAG ACG TCG CCA TGG CAG TCT CCC TGC
TTG ATG AGC ATG GGC ATG CGC AGG GTC TGC AGC GGT ACC GTC AGA GGG ACG
 N   Y   S   Y   P   Y   A   S   P   P   Q   T   S   P   W   Q   S   P   C
         T   L       R   T   R   V   A   R   V   P   D   V   R   T   S   P   A
     L                       P           P       Q                           L   R
                                                  918
GTG TCT CCC AAG ACC ACG GAC CCC GAG GGC TTT CCC CGC GGG NTG GGG GCC
CAC AGA GGG TTC TGC TGC CTG CTC GGG CTC CCG AAA GGG GCG CCC NAC CCC CGG
 V   S   P   K   T   T   D   P   E   G   F   P   R   G       G   A
 C   L   P   R   T   R   T   P   R   A   L   P   A   G   W           G   P
 V   S   Q   D   H   G   P   R   G   L   S   P   R       G               R   L
                                                  972
TGC ACA CTG CTG GGT TCC CCC CAG CAC TCC GTG AGG TGG AGG TCG CCC CGC GCC AGC
ACG TGT GAC CTC TCG AGG GGC GTC GTG AGG CAC TCC ACC TGG AGC TCG CCC CGG TCG
 C   T   L   L   G   S   P   Q   H   S   V   R   W   R   S   P   R   A   S
 A   H   C   W   V   P   P   R   T   P               G   G   V   P   A   P   A
     T               G   L   P   A   L   R   E   V   E   L   A   S   L   P   R
                                                  1026
GTC ACT GAG GAG AGC TGG CTG GGT CCA GCC CGG TCC AGA CCC CGC GCC CCT TGC
CAG TGA CTC CTC TCG ACC GAC CCA GGT CGG GCC AGG TCT GGG CGC GCG GGA ACG
 V   T   E   E   S   W   L   G   P   A   R   S   R   P   R   A   P   C
 S   L   R   R   A   G   L   V   Q   P   G   P   D   P   A   R   P   L   A
     H       G   E   L   A   G   W   V   C   P   L   Q   T   R   V   P       Q
```

```
                                                              1296
CAA GAC CAC CCT GGA GCA GCC CGG CTC AGT GGC GCT CAA GGT GGA GCC CGT CGG
GTT CTG GTG GGA CCT CGT GAG CCG TCA CGA GTT CCA CGG CCT CGG GCA GCC
 Q   D   H   P   G   A   A   R   L   S   G   A   Q   G   G   A   R   R
 V   L   V   G   P   R   E   P   S   V   A   L   S   G   V   P   A   A
 K   T   T   L   E   Q   S   A   P   P   W   S   V   A   L   K   R   W   S   G
                                    1350
GGA GGA CCT GGG CAG CCC CCC GGC CGG CGA CTT CGC GCC CGA AGA CTA CTC
CCT CCT GGA CCC GTC GGG GGG CCG GCT GAA GCG CGG GCT TCT GAT GAG
 G   G   P   G   Q   P   P   G   R   R   L   R   A   R   R   L   L
 P   P   G   P   V   G   G   P   A   E   A   R   A   S   D   E
 G   E   D   L   W   A   A   P   P   R   G   R   L   F   S   R   P   K   T   P
                                    1404
CTC TTT CCA GCA CAT CAG GAA GGG CTT CTG CGA CCA GTA CCT GGC CGT GCC
GAG AAA GGT CGT GTA GTC CCC GAA GAC GCT GGT CAT GGA CCG GCA CGG
 L   F   P   A   H   Q   E   G   L   L   R   P   V   P   G   R   A
 E   K   G   R   V   V   P   E   D   A   G   H   G   P   A   R
 L   S   F   Q   H   I   R   K   G   F   C   D   Q   Y   L   A   V   P   C   R
                                    1458
GCA GCT CCC CTA CCA GTG GCG AAG CCC TTC TCC CCT ACG TCC TAC ATG
CGT CGA GGG GAT GGT CAC CGC TTC GGG GAC AGG TGC AGG ATG TAC
 A   A   P   L   P   V   A   K   P   F   S   P   T   S   Y   M
 R   R   G   D   G   H   R   F   G   D   R   C   R   M   Y
 A   Q   L   P   Y   Q   W   R   K   P   S   P   T   S   Y   P   L   Y   H   E
```

FIG. 1G

```
       1485                                                              1512
AGC CCG ACC CTG CCC GCC CTG GAC TGG CAG CTG CCG TCC CAC TCA GGC CCG TAT
 S   P   T   L   P   A   P   W   Q   S   A   A   V   R   P   S   H   S   G   P   Y
TCG GGC GAC TGG GGG CGG GAC CTG ACC GTC GAC GGC GTG AGT CCG GGC ATA
                 A   R   D   P   L   A   W   T   G   L   D   W   Q   L   P   R   M 1539                                                              1566
GAG CTT CGG ATT GAG GTG CAG CCC AAG TCC CAC CAC CGA GCC CAC TAC GAG ACG
 E   L   R   I   E   V   Q   P   K   S   H   H   R   A   H   Y   E   T
CTC GAA GCC TAA CTC CAC GTC GGG TTC AGG GTG GTG GCT CGG ATG CTC TGC
 E   L   F   R   I   E   V   C   Q   S   P   A   V   T   H   T   R   R
 S           A                       A   S   P   T   P   S   P   R   D 1593                                                              1620
GAG GGC AGC CGG GGG GCC GTG TCG AAG GCG TCG GCC GGA GGA CAC CCC ATC GTG CAG
 E   G   S   R   G   A   V   S   K   A   S   A   G   G   H   P   I   V   Q
CTC CCG TCG GCC CCC CGG CAC TTC CGC AGC CGG CCT GTG TAG CAC GTC
         R   G   G   A   P   R   V   C   A   R   R   V   G   H   D   T   P   H   R 1647                                                              1674
CTG CAT GGC TAC TTG GAG AAT GAG CCG CTG ATG CTG CAG CTT TTC ATT GGG ACG
 L   H   G   Y   L   E   N   E   P   L   M   L   Q   L   F   I   G   T
GAC GTA CCG ATG AAC CTC TTA CTC GGC GAC TAC GTC GAA AAG TAA CCC TGC
     M   A   L   W   T   L   E   N   M   S   R   A   A   D   A   S   F   S   L   G   R
                 Y                                   C   C   A   A       H   W   D   G
```

FIG. 1H

```
                                                      1728
GCG GAC GAC CGC CTG CGC CCG GCC TTC TAC CAG GTG CAC CGC ATC ACA
CGC CTG CTG GCG GAC GCG GGC GTG CGG AAG ATG GTC CAC GCG TAG TGT
 A   D   D   R   L   R   P   A   F   Y   Q   V   H   R   I   T
 R   T   A   P   P   A   R   L   L   P   S   T   R   C   T   A   S   Q
 G                                                             H   R

1782
GGG AAG ACC GTG TCC ACC AGC CAC GAG GCT ATC CTC TCC AAC ACC AAA GTC
CCC TTC TGG CAC AGG TGG TCG GTG CTC CGA TAG GAG AGG TTG TGG TTT CAG
 G   K   T   V   S   T   S   H   E   A   I   L   S   N   T   K   V
 R   P   C   P   P   H   Q   P   A   T   R   G   Y   P   T   P   K   S
 E   D   R   V                                                     Q   P

1836
CTG GAG ATC CCA CTC CCG GAG AAC ATG CGA GCC GTC ATT GAC TGT GCC
GAC CTC TAG GGT GAG GGC CTC TTG TAC GCT CGG CAG TAA CTG ACA CGG
 L   E   I   P   L   P   E   N   M   R   A   V   I   D   C   A
 W   R   S   H   S   C   R   T   S   M   R   A   V   S   L   T   V   P
 G                                                             L   C   R

1890
GGA ATC CTG AAA CTC AGA AAC TCC GAC ATT GAA CTT CGG AAA GGA GAG ACG GAC
CCT TAG GAC TTT GAG TCT TTG AGG CTG TAA CTT GAA GCC TTT CCT CTC TGC CTG
 G   I   L   K   L   R   N   S   D   I   E   L   R   K   G   E   T   D
 E   S   P   T   Q   T   P   L   R   H   T   L   N   F   G   R   R   T
 N   P   E                                                      S   E   R   R   D   G   H

```
                                                                    2160
TCC AAG GTC ATT TTC GTG GAG AAA CCA GAT GGC CAC CAT GTC TGG GAG ATG
AGG TTC CAG TAA AAG CAC CTC CGG TTT CGG GGT CTA CCG GTA CAG ACC CTC TAC
 S   K   V   I   F   V   E   K   P   D   G   H   H   V   W   E   M
 P   R   Q   *   K   H   L   R   F   R   G   L   P   V   Q   T   L   Y
2133

2214
GAA GCG AAA ACT GAC CGG GAC CTG TGC AAG CCG AAT TCT CTG GTG GAG ATC
CTT CGC TTT TGA CTG GCC CTG GAC ACG TTC GGC TTA AGA GAC CAC CTC TAG
 E   A   K   T   D   R   D   L   C   K   P   N   S   L   V   E   I
 K   R   K   *   L   T   G   R   D   L   W   G   L   W   G   D   P
2187                                    S   R   I   L   W   G   L
                                        Q   A   E   F   S   R   D   P

2268
CCG CCA TTT CGG AAT CAG AGG ATA ACC AGC CCC GTT CAC GTC AGT TTC TAC GTC
GGC GGT AAA GCC TTA GTC TCC TAT TGG TCG GGG CAA GTG CAG TCA AAG ATG CAG
 P   P   F   R   N   Q   R   I   T   S   P   V   H   V   S   F   Y   V
 R   A   I   S   E   D   N   Q   P   R   S   Q   F   L   R   L
2241                                        P   A   F   H   V   S   T   S

2322
TGC AAC GGG AAG AGA AAG CGA AGC CAG TAC CAG CGT TTC ACC TAC CTT CCC GCC
ACG TTG CCC TTC TCT TTC GCT TCG GTC ATG GTC GCA AAG TGG ATG GAA GGG CGG
 C   N   G   K   R   K   R   S   Q   Y   Q   R   F   T   Y   L   P   A
 A   T   G   R   E   K   A   K   P   V   P   A   F   H   L   P   S   R   Q
2295
```

FIG. 1K

```
2349
AAC GGT AAC GCC ATC TTT CTA ACC GTA AGC CGT GAA CAT GAG CGC GTG GGG TGC
 N   G   N   A   I   F   L   T   V   S   R   E   H   E   R   V   G   C
TTG CCA TTG CGG TAG AAA GAT TGG GCA TCG GCA CTT GTA CTC GCG CAC CCC ACG
                                                                           2376
                 T   P   H   S   N   R   K   P   A   V   N   E   S   A   V   L
 R

2403
TTT TTC TAA AGA CGC AGA AAC GAC GTC GCC GTA AAG CAG CGT GGC GTG CAC
 F   F   *   R   R   T   E   D   V   A   V   K   Q   R   G   V   H
AAA AAG ATT TCT GCG TCT CTG TTG CAT CAG CGG CAT TTC GTC GCA CCG ACC GTG
 F   S   L   K   R   D   A   E   T   Q   K   S   R   R   R   A   W   R   V   A   H
                                              2430
```

STOP CODON USED BY TRANSFECTED cDNA

```
2457
ATT TAA CTG TGT GAT GTC CGT TAG TGA GAC CGA GCC ATC GAT GCC CTG AAA AGG
 I   *   L   C   D   V   R   *   *   D   R   A   I   D   A   L   K   R
TAA ATT GAC ACA CTA CAG GCA ATC ACT CTG GCT CGG TAG CGG GAC TTT TCC
                                              2484
     L       M   C   V   S   V   R   D   R   A   I   P   S   H   C   P   E   K   G   E

2511
AAA GGA AAA GGG AAG CTT CGG ATC GAT TTT CCT GAN NCT GTT GGG GGT GGG GGG
 K   G   K   G   K   L   R   I   D   F   P   X                L   G   V   G   G   G
TTT CCT TTC CCC TTC GAA GCC TAG CTA AAA GGA CTN NGA CAA CCC CCA CCC CCC
                                              2538
 F   P   F   S                                                  C   W   G
 K   R   K   R   E   A   S   D   R   F   S
```

FIG. 1L

```
                                          2592
GCG GGG GTT GCA TAC TCA GAT AGT CAC GGT TAT TTT GCT TCT TGC GAA TGT ATA
CGC CCC CAA CGT ATG AGT CTA TCA GTG CCA ATA AAA CGA ACG CTT ACA TAT
 A   G   V   A   Y   S   D   S   H   G   Y   F   A   S   C   E   C   I
 R   G   L   Q   R   I   V   T   V   L   I   F   L   L   R   M   Y   N
   G       C               S
2565
                                          2646
ACA GCN AAG GGG AAA ACA TGG CTC TTC TGC TCC AAA AAA CTG AGG GGG TCC TGG
TGT CGN TTC CCC TTT TGT ACC GAG AAG ACG AGG TTT TTT GAC TCC CCC AGG ACC
 T   A   K   G   K   T   W   L   F   C   S   K   K   L   R   G   S   W
 Q   R   N   G   E   N   M   A   L   L   C   F   C   N   T   E   G   P   G
 S                                           Q   K           V   L
2619
                                          2700
TGT GCA TTT GCA CCC TAA AGC TGC TTA CGG TGA AAA AGG AAA TAG GTA TAG CTA
ACA CGT GGG ATT TCG ACG AAT GCC ACT TTT CCG ACT TTT ATC CAT ATC GAT
 C   A   F   A   P   K   S   C   L   R   *   K   G   K   *   V   *   L
 V   H   L   H   P   L   S   A   L   T   V   K   R   Q   I   G   Y
 C   I   C       T   L   K   A   L   L   T                   G
2673
                                          2727
TTT TGC AGG CAC CTT TAG GAA TAA ACT TTG CTT TTA AAA AA
AAA ACG TCC GTG GAA ATC TTA AAC TGA AAT TTT TT
 F   C   R   H   L   *   E   *   T   L   L   K   K
 L   Q   T   F   L   R   N   K   L   C   F   K   K
 F   A   P   G   I   N   F   A   F   K   K   K
```

FIG. 1M

NF-AT POLYPEPTIDES AND POLYNUCLEOTIDES

This invention was made in the course of work supported by the U.S. Government and Howard Hughes Medical Institute, which may have certain rights in this invention.

FIELD OF THE INVENTION

The invention provides novel polypeptides which are associated with the transcription complex NF-AT, polynucleotides encoding such polypeptides, antibodies which are reactive with such polypeptides, polynucleotide hybridization probes and PCR amplification probes for detecting polynucleotides which encode such polypeptides, transgenes which encode such polypeptides, homologous targeting constructs that encode such polypeptides and/or homologously integrate in or near endogenous genes encoding such polypeptides, nonhuman transgenic animals which comprise functionally disrupted endogenous genes that normally encode such polypeptides, and transgenic nonhuman animals which comprise transgenes encoding such polypeptides. The invention also provides methods for detecting T cells (including activated T cells) in a cellular sample, methods for treating hyperactive or hypoactive T cell conditions, methods for screening for immunomodulatory agents, methods for diagnostic staging of lymphocyte differentiation, methods for producing NF-AT proteins for use as research or diagnostic reagents, methods for producing antibodies reactive with the novel polypeptides, and methods for producing transgenic nonhuman animals.

BACKGROUND OF THE INVENTION

The immune response is coordinated by the actions of cytokines produced from activated T lymphocytes. The precursors for most T lymphocytes arise in the bone marrow and migrate to the thymus where they differentiate and express receptors capable of interacting with antigen. These differentiated T lymphocytes then migrate to the peripheral lymphoid organs where they remain quiescent until they come in contact with the cognate antigen. The interaction of antigen with the antigen receptor on T lymphocytes initiates an ordered series of pleiotropic changes; a process denoted as T lymphocyte activation. T lymphocyte activation is a 7 to 10 day process that results in cell division and the acquisition of immunological functions such as cytotoxicity and the production of lymphokines that induce antibody production by B lymphocytes and control the growth and differentiation of granulocyte and macrophage precursors. The cytokines produced by activated T lymphocytes act upon other cells of the immune system to coordinate their behavior and bring about an effective immune response.

The initiation of T lymphocyte activation requires a complex interaction of the antigen receptor with the combination of antigen and self-histocompatibility molecules on the surface of antigen-presenting cells. T lymphocytes may also be activated by relatively simple stimuli such as the combination of a calcium ionophore (e.g., ionomycin) and an activator of protein kinase C, such as phorbol myristate acetate (PMA). Several lectins, including phytohemagglutinin (PHA) may also be used to activate T cells (Nowell (1960) Cancer Res. 20: 462).

T lymphocyte activation involves the specific regulation of particular subsets of genes. The transcriptional regulation characteristic of T cell activation begins minutes after the antigen encounter and continues until at least 10 days later. The T lymphocyte activation genes can be grouped according to the time after stimulation at which each gene is transcribed. Early genes are the first subset of T lymphocyte activation genes that is expressed during the activation process. Expression of the early genes triggers the transcriptional modulation of subsequent genes in the activation pathway. Because of the critical role of the T lymphocyte in the immune response, agents that interfere with expression of the early activation genes, such as cyclosporin A and FK506, are effective immunosuppressants.

Transcription of the early genes requires the presence of specific transcription factors, such as NF-AT, which in turn are regulated through interactions with the antigen receptor. These transcription factors are proteins which act through enhancer and promoter elements near the early activation genes to modulate the rate of transcription of these genes. Many of these transcription factors reversibly bind to specific DNA sequences located in and near enhancer elements.

The interleukin-2 (IL-2) gene is a paradigmatic early activation gene. The IL-2 gene product plays a critical role in T lymphocyte proliferation and differentiation. The IL-2 gene is transcriptionally active only in T cells that have been stimulated through the antigen receptor or its associated molecules (Cantrell and Smith (1984) Science 224: 1312). The transcriptional induction of IL-2 in activated T lymphocytes is mediated by a typical early gene transcriptional enhancer that extends from 325 basepairs upstream of the transcriptional start site for the IL-2 gene (Durand et al. (1988) Mol. Cell. Biol. 8: 1715). Other genes known to contain NF-AT recognition sites in their regulatory regions include: γ-interferon, IL-4, GM-CSF, and others. This region, which is referred to herein as the IL-2 enhancer, has been used extensively to dissect the requirements for T lymphocyte activation. An array of transcription factors, including NF-AT, NFkb, AP-1, Oct-1, and a newly identified protein that associates with Oct-1 called OAP-40, bind to sequences in this region (Ullman et al. (1991) Science 254: 558). These different transcription factors act together to integrate the complex requirements for T lymphocyte activation.

Among the group of transcription factors mentioned above, the presence of NF-AT is characteristic of the transcription events involving early activation genes, in that its recognition sequence is able to enhance transcription of linked heterologous genes in activated T cells of transgenic animals (Verweij et al. (1990) J. Biol. Chem. 265: 15788). The NF-AT sequence element is also the only known transcriptional element in the IL-2 enhancer that has no stimulatory effect on transcription in the absence of physiologic activation of the T lymphocyte through the antigen receptor or through treatment of T cells with the combination of ionomycin and PMA. For example, the NF-AT element enhances transcription of linked sequences in T lymphocytes which have had proper presentation of specific antigen by MHC-matched antigen presenting cells or have been stimulated with the combination of ionomycin/PMA, but not in unstimulated T lymphocytes (Durand et al. (1988) op.cit; Shaw et al. (1988) op.cit; Karttunen and Shastri (1991) Proc. Natl. Acad. Sci. USA 88: 3972; Verweij et al. (1990) op.cit). Moreover, the NF-AT sequence element naturally enhances transcription of the IL-2 gene only in activated T lymphocytes.

Other elements within the IL-2 enhancer, for example, the NFkb site or the AP-1 site, activate transcription in response to less specific stimuli, such as tumor necrosis factor α or simply PMA by itself. These compounds do not by themselves activate transcription of the IL-2 gene and other early activation genes, and do not lead to T lymphocyte activation.

Such observations indicate that the expression of certain early genes, such as the interleukin-2 gene may be regulated by the protein complex NF-AT. Data have also indicated that a selective genetic deficiency of NF-AT produces severe combined immunodeficiency (SCID) (Chatilla et al. (1989) *New Engl. J. Med.* 320: 696).

One of the functional sequences in the IL-2 enhancer is a binding site for a multimeric protein complex, designated NF-AT (nuclear factor of activated T lymphocytes), that functions as a transcriptional regulator of IL-2, IL-4, and other early activation genes (Shaw et al. (1988) *Science* 241: 202). The NF-AT transcription complex is formed subsequent to a signal from the antigen receptor. Enhancement of transcription of genes adjacent to the NF-AT recognition site requires that the NF-AT complex bind to the recognition site (Shaw et al. (1988) *op.cit*). Although the molecular makeup of NF-AT is not fully defined, studies have reported that NF-AT can be reconstituted from a ubiquitous nuclear component that requires protein synthesis for induction and a T cell-specific constitutive cytoplasmic component, designated NF-$AT_c$ (Flanagan et al. (1991) *Nature* 352: 803). This cytoplasmic component, NF-$AT_c$, associates with the nucleus in response to calcium signalling in a manner that is inhibited by the immunosuppressive drugs cyclosporin A (CsA) and FK506. The nuclear component of NF-AT can be induced with PMA, is not sensitive to CsA or FK506, and can be seen in cells of non-T cell origin such as HeLa and Cos.

Northrop et al. (1993) *J. Biol. Chem.* 268: 2917 report that the nuclear component of NF-AT contains the phorbol ester-inducible transcription factor, AP-1 (Jun/Fos), and show that antisera to Fos (a component of AP-1) inhibits NF-AT binding to DNA containing a binding site for AP-1. Moreover, Northrop et al. show that NF-AT DNA binding can be reconstituted in vitro using semi-purified AP-1 proteins mixed with cytosol from T lymphocytes, presumably containing NF-$AT_c$. Northrop et al. also report partial purification of NF-$AT_c$ and report a molecular mass range of approximately 94 to 116 kD as estimated by SDS-polyacrylamide gel electrophoresis.

As noted above, cyclosporin A (CsA) and FK506 are capable of acting as immunosuppressants. These agents inhibit T and B cell activation, mast cell degranulation, and other processes essential to an effective immune response (Borel et al. (1976) *Agents Actions* 6: 468; Sung et al. (1988) *J. Exp. Med.* 168: 1539; Gao et al. *Nature* 336: 176). In T lymphocytes, these drugs disrupt a step in the signal transduction pathway(s) through which the binding of antigen to the T cell antigen receptor produces enhanced transcription of specific cytokine genes involved in the coordination of the immune response. Thus, these agents prevent T lymphocyte activation (Crabtree et al. (1989) *Science* 243: 355; Schreiber et al. (1989) *Science* 251:283; Hohman & Hutlsch (1990) *New Biol.* 2: 663) and act as immunosuppressants.

Putative intracellular receptors for FK506 and CsA have been described and found to be cis-trans prolyl isomerases (Fischer & Bang (1985) *Biochim. Biophys. Acta* 828: 39; Fischer et al. *Nature* 337: 476; Handschumacher et al. (1984) *Science* 226: 544; Lang & Schmid (1988) *Nature* 331: 453; Standaert et al. (1990) *Nature* 346: 671). Binding of the drugs inhibits isomerase activity; however, studies with other prolyl isomerase inhibitors (Bierer et al. (1990) *Science* 250: 556) and analysis of cyclosporin-resistant mutants in yeast suggest that the prevention of T lymphocyte activation results from formation of an inhibitory complex involving the drug and the isomerase (Bierer et al. (1990) *Proc. Natl. Acad. Sci. U.S.A.* 87: 9231; Tropschug et al. (1989) *Nature* 342: 953), and not from inhibition of the isomerase activity per se. CsA and FK-506 prevent T cell proliferation by inhibiting a calcium-dependent signalling event required for the induction of interleukin-2 transcription.

Calcineurin, a calmodulin-dependent protein phosphatase which occurs in various isoforms, has been identified as a critical component of T cell activation through the signal transduction pathway leading to transcriptional activation of NF-AT-dependent genes, such as lymphokine genes (Liu et al. (1991) *Cell* 66: 807; Clipstone and Crabtree (1992) *Nature* 357: 695; O'Keefe et al. (1992) *Nature* 357: 692).

Transcriptional enhancement involving NF-AT recognition sequences is completely blocked in T cells treated with efficacious concentrations of cyclosporin A or FK506, with little or no specific effect on transcriptional enhancement involving recognition sites for other transcription factors, such as AP-1 and NF-KB (Shaw et al.(1988) *op.cit*; Emmel et al. (1989) *Science* 246: 1617; Mattila et al. (1990) *EMBO J.* 9: 4425). This blockage can be overcome, at least partially, by the expression of hyperphysiolgical amounts of calcineurin (Clipstone and Crabtree (1992) *op.cit.*).

Unfortunately, while both cyclosporin A and FK506 are potent immunosuppressive agents, both drugs possess detrimental properties. For example, cyclosporin elicits adverse reactions including renal dysfunction, tremors, nausea and hypertension. Indeed, for many years researchers have attempted to develop superior replacements, with FK506 being the most recent candidate. However, without understanding the mechanisms by which cyclosporin (or FK506) functions at the intracellular level, developing improved immunosuppressants represents an extremely difficult research effort with a limited likelihood of success.

Thus, there exists a significant need to understand the functional basis of T cell activation involving NF-AT, particularly with regard to the mechanism by which these immunosuppressants such as CsA and FK506 inhibit transcription of the early activation genes. With such knowledge, improved assays for screening drug candidates would be feasible, which could in turn dramatically enhance the search process. Modulation of the immune system, especially modulation of T cell activation, also may be effected by directly altering the amount or activity of NF-AT. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides several novel methods and compositions for modulating the immune response and for screening for modulators of the immune response. These methods utilize polynucleotide sequences encoding NF-$AT_c$ recombinant proteins and complementary polynucleotides which are substantially identical to NF-$AT_c$ polynucleotide sequences.

In one aspect of the invention, NF-$AT_c$ polypeptides and compositions thereof are provided. NF-$AT_c$ polypeptides comprise polypeptide sequences which are substantially identical to a sequence shown in FIG. 1 (SEQ. ID NOS: 1 and 2) or a cognate NF-$AT_c$ gene sequence.

Nucleic acid sequences encoding NF-$AT_c$ are provided. The characteristics of the cloned sequences are given, including the nucleotide and predicted amino acid sequence in FIG. 1 (SEQ. ID NOS: 1and 2). Polynucleotides comprising these sequences can serve as templates for the recombinant expression of quantities of NF-AT$_c$ polypeptides, such as human NF-AT$_c$ and murine NF-AT$_c$. Polynucleotides comprising these sequences can also serve as probes for nucleic acid hybridization to detect the transcription and mRNA abundance of NF-AT$_c$ mRNA in individual lymphocytes (or other cell types) by in situ hybridization, and in specific lymphocyte populations by Northern blot analysis and/or by in situ hybridization (Alwine et al. (1977) *Proc. Natl. Acad. Sci. U.S.A.* 74: 5350) and/or PCR amplification and/or LCR detection. Such recombinant polypeptides and nucleic acid hybridization probes have utility for in vitro screening methods for immunomodulatory agents and for diagnosis and treatment of pathological conditions and genetic diseases, such as transplant rejection reactions, T cell-mediated immune responses, lymphocytic leukemias (e.g., T cell leukemia or lymphoma) wherein NF-AT activity contributes to disease processes, autoimmune disease, arthritis, and the like.

In one embodiment, candidate immunomodulatory agents are identified by their ability to block the binding of a NF-AT$_c$ polypeptide to other components of NF-AT (e.g., AP-1) and/or to block the binding of NF-AT to DNA having an NF-AT recognition site. The DNA preferably includes one or more NF-AT binding sites at which a NF-AT protein complex specifically binds. One means for detecting binding of a NF-AT protein comprising NF-AT$_c$ to DNA is to immobilize the DNA, such as by covalent or noncovalent chemical linkage to a solid support, and to contact the immobilized DNA with a NF-AT protein complex comprising a NF-AT$_c$ polypeptide that has been labeled with a detectable marker (e.g., by incorporation of radiolabeled amino acid). Such contacting is typically performed in aqueous conditions which permit binding of a NF-AT protein to a target DNA containing a NF-AT binding sequence. Binding of the labeled NF-AT to the immobilized DNA is measured by determining the extent to which the labeled NF-AT$_c$ polypeptide is immobilized as a result of a specific binding interaction. Such specific binding may be reversible, or may be optionally irreversible if a cross-linking agent is added in appropriate experimental conditions.

In one aspect, candidate immunomodulatory agents are identified as being agents capable of inhibiting (or enhancing) intermolecular binding between NF-AT$_c$ and other polypeptides which comprise a NF-AT complex (e.g., AP-1, JunB, etc.). The invention provides methods and compositions for screening libraries of agents for the capacity to interfere with binding of NF-AT$_c$ to other NF-AT polypeptide species under aqueous binding conditions. Typically, at least either NF-AT$_c$ and/or another NF-AT polypeptide species is labeled with a detectable label and intermolecular binding between NF-AT$_c$ and other NF-AT polypeptide species is detected by the amount of labeled species captured in NF-AT complexes and the like.

The invention also provides antisense polynucleotides complementary to NF-AT$_c$ sequences which are employed to inhibit transcription and/or translation of the cognate mRNA species and thereby effect a reduction in the amount of the respective NF-AT$_c$ protein in a cell (e.g., a T lymphocyte of a patient). Such antisense polynucleotides can function as immunomodulatory drugs by inhibiting the formation of NF-AT protein required for T cell activation.

In a variation of the invention, polynucleotides of the invention are employed for diagnosis of pathological conditions or genetic disease that involve T cell neoplasms or T cell hyperfunction of hypofunction, and more specifically conditions and diseases that involve alterations in the structure or abundance of NF-AT$_c$ polypeptide, NF-AT$_c$ polynucleotide sequence, or structure of the NF-AT$_c$ gene or flanking region(s).

The invention also provides antibodies which bind to NF-AT$_c$ with an affinity of about at least $1\times10^7 M^{-1}$ and which lack specific high affinity binding for other proteins present in activated T cells. Such antibodies can be used as diagnostic reagents to identify T cells (e.g., activatable T cells) in a cellular sample from a patient (e.g., a lymphocyte sample, a solid tissue biopsy) as being cells which contain an increased amount of NF-AT$_c$ protein determined by standardization of the assay to be diagnostic for activated T cells. Frequently, anti-NF-AT$_c$ antibodies are included as diagnostic reagents for immunohistopathology staining of cellular samples in situ. Additionally, anti-NF-AT$_c$ antibodies may be used therapeutically by targeted delivery to T cells (e.g., by cationization or by liposome/immunoliposome delivery).

The invention also provides NF-AT$_c$ polynucleotide probes for diagnosis of neoplasia or immune status by detection of NF-AT$_c$ mRNA in cells explanted from a patient, or detection of a pathognomonic NF-AT$_c$ allele (e.g., by RFLP or allele-specific PCR analysis). A pathognomonic NF-AT$_c$ allele is an allele which is statistically correlated with the presence of a predetermined disease or propensity to develop a disease. Typically, the detection will be by in situ hybridization using a labeled (e.g., $^{32}$p, $^{35}$s, $^{14}$C, $^{3}$H, fluorescent, biotinylated, digoxigeninylated) NF-AT$_c$ polynucleotide, although Northern blotting, dot blotting, or solution hybridization on bulk RNA or poly A$^+$ RNA isolated from a cell sample may be used, as may PCR amplification using NF-ATC-specific primers. Cells which contain an increased amount of NF-AT$_c$ mRNA as compared to standard control values for cells or cell types other than activated T cells or activatable T cells will be thereby identified as activated T cells or activatable T cells. Similarly, the detection of pathognomonic rearrangements or amplification of the NF-AT$_c$ locus or closely linked loci in a cell sample will identify the presence of a pathological condition or a predisposition to developing a pathological condition (e.g., cancer, genetic disease).

The present invention also provides a method for diagnosing T cell hypofunction of hyperfunction in a human patient, wherein a diagnostic assay (e.g., immunohistochemical staining of fixed lymphocytic cells by an antibody that specifically binds human NF-AT$_c$) is used to determine if a predetermined pathognomonic concentration of NF-AT$_c$ protein or NF-AT$_c$ mRNA is present in a biological sample from a human patient; if the assay indicates the presence of NF-AT$_c$ protein or NF-AT$_c$ mRNA at or above such predetermined pathognomonic concentration, the patient is diagnosed as having T cell hyperfunction or hypofunction condition, or transplant rejection and the like.

All publications and patent applications herein are incorporated by reference to the same extent as if each individual publication or patent application was specifically and individually indicated to be incorporated by reference.

BRIEF DESCRIPTION OF THE FIGURES

FIG. 1A–1M (SEQ. ID NOS: 1and 2) shows the nucleotide sequence of the human NF-AT$_c$ cDNA and the deduced amino acid sequence. N indicates that a seqeunce ambiguity is present.

DEFINITIONS

Figure 2:
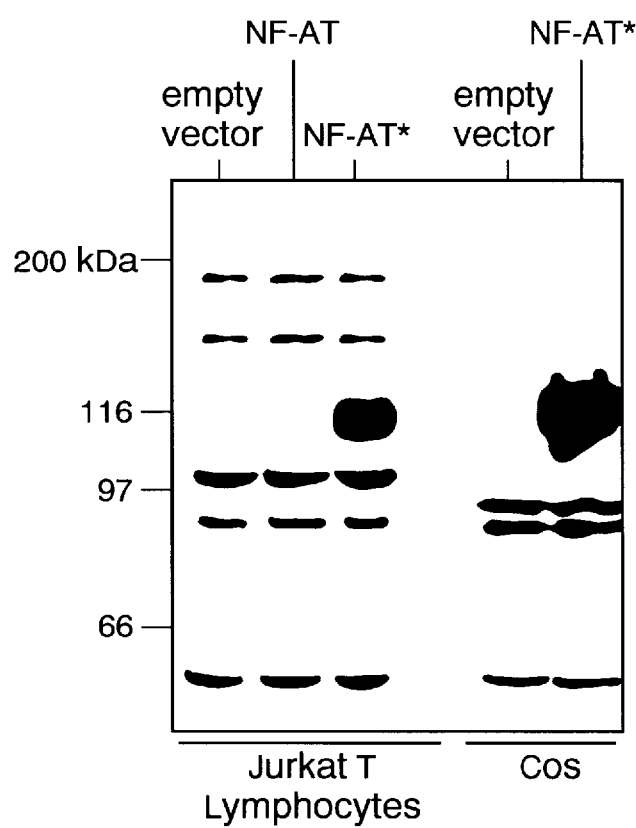
FIG. 2 shows the expression of NF-AT$_c$ protein in T cells (Jurkat) and non-T cells (Cos).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1, or may comprise a complete CDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human NF-AT$_c$ polynucleotide sequence shown in FIG. 1 or the full-length murine or bovine NF-AT$_c$ cDNA sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "NF-AT$_c$ native protein" and "full-length NF-AT$_c$ protein" as used herein refers to a a naturally-occurring NF-AT$_c$ polypeptide corresponding to the deduced amino acid sequence shown in FIG. 1 or corresponding to the deduced amino acid sequence of a cognate full-length cDNA. Also for example, a native NF-AT$_c$ protein present in naturally-occurring lymphocytes which express the NF-AT$_c$ gene are considered full- length NF-AT$_c$ proteins.

The term "INF-AT$_c$ fragment" as used herein refers to a polypeptide that has an amino-terminal and/or carboxy-terminal deletion, but where the remaining amino acid sequence is identical to the corresponding positions in the NF-AT$_c$ sequence deduced from a full-length cDNA sequence (e.g., the cDNA sequence shown in FIG. 1). NF-AT$_c$ fragments typically are at least 14 amino acids long, preferably at least 20 amino acids long, usually at least 50 amino acids long or longer.

The term "NF-AT$_c$ analog" as used herein refers to polypeptides which are comprised of a segment of at least 25 amino acids that has substantial identity to a portion of the deduced amino acid sequence shown in FIG. 1 , and which has at least one of the following properties: (1) binding to other NF-AT proteins (e.g., AP-1) under suitable binding conditions, or (2) ability to localize to the nucleus upon T cell activation. Typically, NF-AT$_c$ analog polypeptides comprise a conservative amino acid substitution (or addition or deletion) with respect to the naturally-occurring sequence. NF-AT$_c$ analogs typically are at least 20 amino acids long, preferably at least 50 amino acids long or longer, most usually being as long as full-length naturally-occurring NF-AT$_c$ (e.g., as shown in FIG. 1). Some NF-AT$_c$ analogs may lack biological activity but may still be employed for various uses, such as for raising antibodies to NF-AT$_c$ epitopes, as an immunological reagent to detect and/or purify α-NF-AT$_c$ antibodies by affinity chromatography, or as a competitive or noncompetitive agonist, antagonist, or partial agonist of native NF-AT$_c$ protein function.

The term "NF-AT$_c$ polypeptide" is used herein as a generic term to refer to native protein, fragments, or analogs of NF-AT$_c$. Hence, native NF-AT$_c$, fragments of NF-AT$_c$, and analogs of NF-AT$_c$ are species of the NF-AT$_c$ polypeptide genus. Preferred NF-AT$_c$ polypeptides include: the human full-length NF-AT$_c$ protein comprising the polypeptide sequence shown in FIG. 1, or polypeptides consisting essentially of a sequence shown in Table II.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate murine gene to the human NF-AT$_c$ gene is the murine gene which encodes an expressed protein which has the greatest degree of sequence identity to the human NF-AT$_c$ protein and which exhibits an expression pattern similar to that of the human NF-AT$_c$ (e.g., expressed in T lineage cells). Preferred cognate NF-AT$_c$ genes are: rat NF-AT$_c$, rabbit NF-AT$_c$, canine NF-AT$_c$, nonhuman primate NF-AT$_c$, porcine NF-AT$_c$, bovine NF-AT$_c$, and hamster NF-AT$_c$.

The term "NF-AT$_c$-dependent gene" is used herein to refer to genes which: (1) have a NF-AT binding site (a site which can be specifically footprinted by NF-AT under suitable binding conditions) within about 10 kilobases of the first coding sequence of said gene, and (2) manifest an altered rate of transcription, either increased or decreased, from a major or minor transcriptional start site for said gene, wherein such alteration in transcriptional rate correlates with the presence of NF-AT$_c$ polypeptide in NF-AT complexes, such as in an activated T cell.

The term "altered ability to modulate" is used herein to refer to the capacity to either enhance transcription or inhibit transcription of a gene; such enhancement or inhibition may be contingent on the occurrence of a specific event, such as T cell stimulation. This alteration will be manifest as an inhibition of the transcriptional enhancement of the IL-2 gene that normally ensues following T cell stimulation. The altered ability to modulate transcriptional enhancement or inhibition may affect the inducible transcription of a gene, such as in the just-cited IL-2 example, or may effect the basal level transcription of a gene, or both.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as immunomodulatory agents (e.g., immunosuppressants) by inclusion in screening assays described hereinbelow.

The term "candidate immunomodulatory agent" is used herein to refer to an agent which is identified by one or more screening method(s) of the invention as a putative immuomodulatory agent. Some candidate immunomodulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, 131I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the terms "pathognomonic concentration", "pathognomonic amount", and "pathognomonic staining pattern" refer to a concentration, amount, or localization pattern, respectively, of a NF-AT$_c$ protein or mRNA in a sample, that indicates the presence of a hypofunctional or hyperfunctional T cell condition or a predisposition to developing a disease, such as graft rejection. A pathognomonic amount is an amount of a NF-AT$_c$ protein or NF-AT$_c$ mRNA in a cell or cellular sample that falls outside the range of normal clinical values that is established by prospective and/or retrospective statistical clinical studies. Generally, an individual having a neoplastic disease (e.g., lymphocytic leukemia) or T cell-mediated immune response will exhibit an amount of NF-AT$_c$ protein or mRNA in a cell or tissue sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (PCR Technology: Principles and Applications for DNA Amplification ed. HA Erlich, Freeman Press, New York, N.Y. (1992); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, eds. McPherson, Quirkes, and Taylor, IRL Press, Oxford; and U.S. Pat. No. 4,683,202, which are incorporated herein by reference).

Commonly assigned application U.S. Ser. No. 07/749,385 filed 22 Aug. 1991 is incorporated herein by reference.

Cloning of NF-AT$_c$ Polynucleotides

Genomic or cDNA clones encoding NF-AT$_c$ may be isolated from clone libraries (e.g., available from Clontech, Palo Alto, Calif.) using hybridization probes designed on the basis of the nucleotide sequences shown in FIG. 1 and using conventional hybridization screening methods (e.g., Benton WD and Davis RW (1977) Science 196: 180; Goodspeed et al. (1989) Gene 76: 1; Dunn et al. (1989) J. Biol. Chem. 264: 13057). Where a cDNA clone is desired, clone libraries containing cDNA derived from T cell mRNA is preferred. Alternatively, synthetic polynucleotide sequences corresponding to all or part of the sequences shown in FIG. 1 may be constructed by chemical synthesis of oligonucleotides. Additionally, polymerase chain reaction (PCR) using primers based on the sequence data disclosed in FIG. 1 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used.

It is apparent to one of skill in the art that nucleotide substitutions, deletions, and additions may be incorporated into the polynucleotides of the invention. Nucleotide sequence variation may result from sequence polymorphisms of various NF-AT$_c$ alleles, minor sequencing errors, and the like. However, such nucleotide substitutions, deletions, and additions should not substantially disrupt the ability of the polynucleotide to hybridize to one of the polynucleotide sequences shown in FIG. 1 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1), wherein the probe preferentially hybridizes to the specific target such that, for example, a single band corresponding to NF-AT$_c$ mRNA (or bands corresponding to multiple alternative splicing products of the NF-AT$_c$ gene) can be identified on a Northern blot of RNA prepared from a suitable cell source (e.g., a T cell expressing NF-AT$_c$). Polynucleotides of the invention and recombinantly produced NF-AT$_c$, and fragments or analogs thereof, may be prepared on the basis of the sequence data provided in FIG. 1 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology. Volume* 152, *Guide to Molecular Cloning Techniques* (1987), Academic Press, Inc., San Diego, Calif., which are incorporated herein by reference.

NF-AT$_c$ polynucleotides may be short oligonucleotides (e.g., 25–100 bases long), such as for use as hybridization probes and PCR (or LCR) primers. NF-AT$_c$ polynucleotide sequences may also comprise part of a larger polynucleotide (e.g., a cloning vector comprising a NF-AT$_c$ clone) and may be fused, by polynucleotide linkage, in frame with another polynucleotide sequence encoding a different protein (e.g., glutathione S-transferase or β-galactosidase) for encoding expression of a fusion protein. Typically, NF-AT$_c$ polynucleotides comprise at least 25 consecutive nucleotides which are substantially identical to a naturally-occurring NF-AT$_c$ sequence (e.g., FIG. 1), more usually NF-AT$_c$ polynucleotides comprise at least 50 to 100 consecutive nucleotides which are substantially identical to a naturally-occurring NF-AT$_c$ sequence. However, it will be recognized by those of skill that the minimum length of a NF-AT$_c$ polynucleotide required for specific hybridization to a NF-AT$_c$ target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

For example but not limitation, suitable hybridization probes for detecting and/or quantifying the presence of NF-AT$_c$ mRNA in a sample generally comprise at least one, preferably at least two, and more preferably all of the following human NF-AT$_c$ sequences shown in Table I, or their complements:

TABLE I

Selected Human NF-ATC Polynucleotide Sequences

5'-TTC CTC CGG GGC GCG CGG CGT GAG CCC GGG GCG AGG-3' (SEQ. ID NO.3);
5'-CAG CGC GGG GCG GCC ACT TCT CCT GTG CCT CCG CCC GCT GCT-3' (SEQ. ID NO.4);
5'-GCC GCG CGG ATG CCA AGC ACC AGC TTT CCA GTC CCT TCC AAG-3' (SEQ. ID NO.5);
5'-CCA ACG TCA GCC CCG CCC TGC CGC TCC CCA CGG CGC ACT CCA-3' (SEQ. ID NO.6);
5'-TTC AGA CCT CCA CAC CGG GCA TCA TCC CGC CGG CGG-3' (SEQ. ID NO.7);
5'-GCC ACA CCA GGC CTG ATG GGG CCC CTG CCC TGG AGA GTC CTC-3' (SEQ. ID NO.8);
5'-AGT CTG CCC AGC CTG GAG GCC TAC AGA GAC CCC TCG TGC CTG-3' (SEQ. ID NO.9);
5'-GTG TCT CCC AAG ACC ACG GAC CCC GAG GAG GGC TTT CCC-3' (SEQ. ID NO.10);
5'-AGC TGG CTG GGT GCC CGC TCC TCC AGA CCC GCG TCC CCT TGC-3' (SEQ. ID NO.11);
5'-TAC AGC CTC AAC GGC CGG CAG CCG CCC TAC TCA CCC CAC CAC-3' (SEQ. ID NO.12);
5'-GAC CAC CGA CAG CAG CCT GGA CCT GGG AGA TGG CGT CCC TGT-3' (SEQ. ID NO.13);
5'-CCT GGG CAG CCC CCC GCC CCC GGC CGA CTT CGC GCC CGA AGA-3' (SEQ. ID NO.14);
5'-GCT CCC CTA CCA GTG GCG AAG CCC AAG CCC CTG TCC CCT ACG-3' (SEQ. ID NO.15);
5'-CTT CGG ATT GAG GTG CAG CCC AAG TCC CAC CAC CGA GCC CAC-3' (SEQ. ID NO.16);
5'-CAT GGC TAC TTG GAG AAT GAG CCG CTG ATG CTG CAG CTT TTC-3' (SEQ. ID NO.17);
5'-AAG ACC GTG TCC ACC ACC AGC CAC GAG GCT ATC CTC TCC AAC-3' (SEQ. ID NO.18);
5'-TCA GCT CAG GAG CTG CCT CTG GTG GAG AAG CAG AGC ACG GAC-3' (SEQ. ID NO.19);
5'-AAC GCC ATC TTT CTA ACC GTA AGC CGT GAA CAT GAG CGC G-3' (SEQ. ID NO.20);
5'-AGA AAC GAC GTC GCC GTA AAG CAG CGT GGC GTG TGG CA-3' (SEQ. ID NO.21); and
5'-GCA TAC TCA GAT AGT CAC GGT TAT TTT GCT TCT TGC GAA TG-3' (SEQ. ID NO.22).

Also for example but not limitation, the following pair of PCR primers (amplimers) may be used to amplify murine or human NF-AT$_c$ sequences (e.g., by reverse transcriptase initiated PCR of RNA from NF-AT$_c$ expressing cells):
(forward) 5'-AGGGCGCGGGCACCGGGGCGCGGGCA-GGGCTCGGAG-3' (SEQ. ID NO:23)
(reverse) 5'-GCAAGAAGCAAAATAACCGTGACTATC-TGAGTATGC-3' (SEQ. ID NO:24)
If desired, PCR amplimers for amplifying substantially full-length cDNA copies may be selected at the discretion of the practitioner. Similarly, amplimers to amplify single NF-AT$_c$ exons or portions of the NF-AT$_c$ gene (murine or human) may be selected.

Each of these sequences may be used as hybridization probes or PCR amplimers to detect the presence of NF-AT$_c$ mRNA, for example to diagnose a disease characterized by the presence of an elevated NF-AT$_c$ mRNA level in lymphocytes, or to perform tissue typing (i.e., identify tissues characterized by the expression of NF-AT$_c$ mRNA), and the like. The sequences may also be used for detecting genomic NF-AT$_c$ gene sequences in a DNA sample, such as for forensic DNA analysis (e.g., by RFLP analysis, PCR product length(s) distribution, etc.) or for diagnosis of diseases characterized by amplification and/or rearrangements of the NF-AT$_c$ gene.

Production of NF-AT$_c$ Polypeptides

The nucleotide and amino acid sequences shown in FIG. 1 enable those of skill in the art to produce polypeptides corresponding to all or part of the full-length human NF-AT$_c$ polypeptide sequence. Such polypeptides may be produced in prokaryotic or eukaryotic host cells by expression of polynucleotides encoding NF-AT$_c$, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of NF-AT$_c$ may be prepared by those of skill in the art. Preferred amino- and carboxytermini of fragments or analogs of NF-AT$_c$ occur near boundaries of functional domains. For example, but not for limitation, such functional domains include: (1) domains conferring the property of binding to other NF-AT components (e.g., AP-1), (2) domains conferring the property of nuclear localization in stimulated T lymphocytes, and (3) domains conferring the property of enhancing activation of T cells when expressed at sufficient levels in such cells. Additionally, such functional domains might include: (1) domains conferring the property of binding to RNA polymerase species, (2) domains having the capacity to directly alter local chromatin structure, which may comprise catalytic activities (e.g., topoisomerases, endonucleases) and/or which may comprise structural features (e.g., zinc fingers, histone-binding moieties), and (3) domains which may interact with accessory proteins and/or transcription factors.

One method by which structural and functional domains may be identified is by comparison of the nucleotide and/or amino acid sequence data shown in FIG. 1 to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the NF-AT$_c$ sequences of the invention.

Additionally, computerized comparison of sequences shown in FIG. 1 to existing sequence databases can identify sequence motifs and structural conformations found in other proteins or coding sequences that indicate similar domains of the NF-AT$_c$ protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a NF-AT$_c$ sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in NF-AT$_c$ polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the NF-AT$_c$ fragment. Alternatively, NF-AT$_c$ polypeptides wherein one or more functional domain have been deleted will exhibit a loss of the property normally conferred by the missing fragment.

By way of example and not limitation, the domain conferring the property of nuclear localization and/or interaction with AP-1 may be fused to β-galactosidase to produce a fusion protein that is localized to the nucleus and which can enzymatically convert a chromogenic substrate to a chromophore.

Although one class of preferred embodiments are fragments having amino- and/or carboxy-termini corresponding to amino acid positions near functional domains borders, alternative NF-AT$_c$ fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of NF-AT$_c$ can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native NF-AT$_c$ protein. However, NF-AT$_c$ analogs must comprise a segment of 25 amino acids that has substantial similarity to a portion of the amino acid sequence shown in FIG. 1, respectively, and which has at least one of the requisite functional properties enumerated in the Definitions (supra). Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with calcineurin or phosphorylation or dephosphorylation thereby. NF-AT$_c$ analogs include various muteins of a NF-AT$_c$ sequence other than the naturally-occurring peptide sequence. For example, single or multiple amino acid substitutions (preferably conservative amino acid substitutions) may be made in the naturally-occurring NF-AT$_c$ sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Native NF-AT$_c$ proteins, fragments thereof, or analogs thereof can be used as reagents in DNA binding assays and/or in vitro transcription assays for identifying agents that interfere with NF-AT function, said agents are thereby identified as candidate drugs which may be used, for example, to block T cell activation or treat T cell lymphocytic leukemias. Typically, in vitro DNA binding assays that measure binding of NF-AT to DNA employ double-stranded DNA that contains an array of one or more NF-AT recognition sites (as defined by specific footprinting of native NF-AT protein). The DNA is typically linked to a solid substrate by any of various means known to those of skill in the art; such linkage may be noncovalent (e.g., binding to a highly charged surface such as Nylon 66) or may be by covalent bonding (e.g., typically by chemical linkage involving a nitrogen position in a nucleotide base, such as diazotization). $NF-AT_c$ polypeptides are typically labeled by incorporation of a radiolabeled amino acid. The labeled $NF-AT_c$ polypeptide, usually reconstituted with an NF-AT nuclear component (e.g., AP-1 activity) to form an NF-AT complex, is contacted with the immobilized DNA under aqueous conditions that permit specific binding in control binding reactions with a binding affinity of about $1\times10^6 M^{-1}$ or greater (e.g., 10–250 mM NaCl or KCl and 5–100 mM Tris HCl pH 5–9, usually pH 6–8), generally including $Zn^{+2}$ and/or $Mn^{+2}$ and/or $Mg^{+2}$ in the nanomolar to micromolar range (1 nM to 999 μM). Specificity of binding is typically established by adding unlabeled competitor at various concentrations selected at the discretion of the practitioner. Examples of unlabeled protein competitors include, but are not limited to, the following: unlabeled $NF-AT_c$ polypeptide, bovine serum albumin, and nuclear protein extracts. Binding reactions wherein one or more agents are added are performed in parallel with a control binding reaction that does not include an agent. Agents which inhibit the specific binding of $NF-AT_c$ polypeptides to DNA, as compared to a control reaction, are identified as candidate immunomodulatory drugs. Also, agents which prevent transcriptional modulation by NF-AT in vitro are thereby identified as candidate immunomodulatory drugs.

In addition to $NF-AT_c$ polypeptides consisting only of naturally-occuring amino acids, $NF-AT_c$ peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human $NF-AT_c$, but have one or more peptide linkages optionally replaced by a linkage selected from the group consisting of: —CH₂NH—, —CH₂S—, —CH₂—CH₂—, —CH=CH— (cis and trans), —COCH₂—, —CH(OH)CH₂—, and —CH₂SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH₂NH—, CH₂CH₂—); Spatola, A. F. et al., *Life Sci* (1986) 38:1243–1249 (—CH₂—S); Hann, M. M., *J Chem Soc Perkin Trans I* (1982) 307–314 (—CH—CH—, cis and trans); Almquist, R. G. et al., *J Med Chem* (1980) 23:1392–1398 (—COCH₂—); Jennings-White, C. et al., *Tetrahedron Lett* (1982) 23:2533 (—COCH₂—); Szelke, M. et al., European Appln. EP 45665 (1982) CA: 97:39405 (1982) (—CH(OH)CH₂—); Holladay, M.W. et al., *Tetrahedron Lett* (1983) 24:4401–4404 (—C(OH)CH₂—); and Hruby, V. J., *Life Sci* (1982) 31:189–199 (—CH₂—S—); each of which is incorporated herein by reference. A particularly preferred non-peptide linkage is —CH₂NH—.

Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic. Peptidomimetics of $NF-AT_c$ may be used as competitive or noncompetitive agonists or antagonists of $NF-AT_c$ function. For example, a $NF-AT_c$ peptidomimetic administered to a stimulated T cell containing $NF-AT_c$ and may compete with the naturally-occurring $NF-AT_c$ and reduce NF-AT activity. Alternatively, an $NF-AT_c$ peptidomimetic administered to a T cell lacking $NF-AT_c$ may induce T cell activation or the like.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

The amino acid sequences of $NF-AT_c$ polypeptides identified herein will enable those of skill in the art to produce polypeptides corresponding to $NF-AT_c$ peptide sequences and sequence variants thereof. Such polypeptides may be produced in prokaryotic or eukaryotic host cells by expression of polynucleotides encoding a $NF-AT_c$ peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology. Volume 152, Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins*, Wiley Publishing, which are incorporated herein by reference).

Production and Applications of α-$NF-AT_c$ Antibodies

Native $NF-AT_c$ proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of human NF-AT$_c$ can be injected into a rat along with an adjuvant following immunization protocols known to those of skill in the art so as to generate an immune response. Typically, approximately at least 1–50 μg of a NF-AT$_c$ fragment or analog is used for the initial immunization, depending upon the length of the polypeptide. Alternatively or in combination with a recombinantly produced NF-AT$_c$ polypeptide, a chemically synthesized peptide having a NF-AT$_c$ sequence (e.g., peptides exemplified in Table II, infra) may be used as an immunogen to raise antibodies which bind a NF-AT$_c$ protein, such as the native human NF-AT$_c$ polypeptide having the sequence shown essentially in FIG. 1 or the native human NF-AT$_c$ polypeptide isoform. Immunoglobulins which bind the recombinant fragment with a binding affinity of at least $1 \times 10^7 M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced NF-AT$_c$ polypeptide (or chemically synthesized NF-AT$_c$ polypeptide) with an affinity of at least $1 \times 10^6 M^{-1}$. Animals other than mice and rats may be used to raise antibodies; for example, goats, rabbits, sheep, and chickens may also be employed to raise antibodies reactive with a NF-AT$_c$ protein. Transgenic mice having the capacity to produce substantially human antibodies also may be immunized and used for a source of α-NF-AT$_c$ antiserum and/or for making monoclonal-secreting hybridomas.

Bacteriophage antibody display libraries may also be screened for binding to a NF-AT$_c$ polypeptide, such as a full-length human NF-AT$_c$ protein, a NF-AT$_c$ fragment (e.g., a peptide having a sequence shown in Table II, infra), or a fusion protein comprising a NF-AT$_c$ polypeptide sequence of at least 14 contiguous amino acids as shown in FIG. 1 or a polypeptide sequence of Table II (infra). Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a NF-AT$_c$ polypeptide that is immobilized (e.g., by covalent linkage to a chromatography resin to enrich for reactive phage by affinity chromatography) and/or labeled (e.g., to screen plaque or colony lifts).

NF-AT$_c$ polypeptides which are useful as immunogens, for diagnostic detection of α-NF-AT$_c$ antibodies in a sample, for diagnostic detection and quantitation of NF-AT$_c$ protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants. Preferred immunogens comprise at least one NF-AT$_c$ polypeptide sequence shown in Table II, either as a discrete peptide or as part of a fusion polypeptide (e.g., with a β-galactosidase or glutathione S-transferase sequence). NF-AT$_c$ immunogens comprise at least one, typically several of such immunogenic epitopes.

For some applications of these antibodies, such as identifying immunocrossreactive proteins, the desired antiserum or monoclonal antibody(ies) is/are not monospecific. In these instances, it may be preferable to use a synthetic or recombinant fragment of NF-AT$_c$ as an antigen rather than using the entire native protein. More specifically, where the object is to identify immunocrossreactive polypeptides that comprise a particular structural moiety, such as a DNA-binding domain, it is preferable to use as an antigen a fragment corresponding to part or all of a commensurate structural domain in the NF-AT$_c$ protein. Production of recombinant or synthetic fragments having such defined amino- and carboxy-termini is provided by the NF-AT$_c$ sequences shown in FIG. 1.

If an antiserum is raised to a NF-AT$_c$ fusion polypeptide, such as a fusion protein comprising a NF-AT$_c$ immunogenic epitope fused to β-galactosidase or glutathione S-transferase, the antiserum is preferably preadsorbed with the non-NF-AT$_c$ fusion partner (e.g, β-galactosidase or glutathione S-transferase) to deplete the antiserum of antibodies that react (i.e., specifically bind to) the non-NF-AT$_c$ portion of the fusion protein that serves as the immunogen. Monoclonal or polyclonal antibodies which bind to the human and/or murine NF-AT$_c$ protein can be used to detect the presence of human or murine NF-AT$_c$ polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured NF-AT$_c$ epitopes and may be identified visually or by other optical means with a labeled second antibody or labeled *Staphylococcus aureus* protein A by methods known in the art. Frequently, denatured NF-AT$_c$ will be used as the target antigen so that more epitopes may be available for binding.

TABLE II

Selected Human NF-AT$_c$ Antigen Peptides

-FLRGARREPGARAVF- (SEQ. ID NO:25);
-GAATSPVPPPAAPLPAAAAR- (SEQ ID NO.26);
-NAIFLTVSREHERVGC- (SEQ ID NO.27);
-AKTDRDLCKPNSLVVEIPPFRN- (SEQ ID NO.28)
-GILKLRNSDIELRKGETD- (SEQ ID NO.29);
-LHGYLENEPLMLQLFIGT- (SEQ ID NO.30);
-EVQPKSHHRAHYETEGSR- (SEQ ID NO. 31).

Such NF-AT$_c$ sequences as shown in Tables II maybe used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. A preferred NF-AT$_c$ polypeptide comprises the following amino acids sequences:
-FLRGARREPGARAVF-;
-GAATSPVPPPAAPLPAAAAR-;
-NAIFLTVSREHERVGC-;
-AKTDRDLCKPNSLVVEIPPFRN-
and may comprise other intervening and/or terminal sequences; generally such polypeptides are less than 1000 amino acids in length, more usually less than about 500 amino acids in length; often spacer peptide sequences or terminal peptide sequences, if present, correspond to naturally occurring polypeptide sequences, generally mammalian polypeptide sequences. One application of the preferred NF-AT$_c$ polypeptide just recited is as a commercial immunogen to raise α-NF-AT$_c$ antibodies in a suitable animal and/or as a commercial immunodiagnostic reagent for quantitative ELISA (e.g., competitive ELISA) or competitive RIA in conjunction with the anti-NF-AT$_c$ antibodies provided by the invention, such as for calibration of standardization of such immunoassays for staging or diagnosis of NF-AT$_c$-expressing lymphocytic leukemias in humans or cell typing or identification of T cells (such as activated T cells and/or activatable T cells). The preferred NF-AT$_c$ polypeptide just recited will find many other uses in addition to serving as an immunogen or immunological reagent. One or more of the above-listed sequences may be incorporated into a fusion protein with a fusion partner such as human serum albumin, GST, etc. For such fusion proteins in excess of 1000 amino acids, deletions in the fusion partner (albumin) moiety may be made to bring the size to about 1000 amino acids or less, if desired.

In some embodiments, it will be desirable to employ a polyvalent NF-AT$_c$ antigen, comprising at least two NF-AT$_c$ immunogenic epitopes in covalent linkage, usually in peptide linkage. Such polyvalent NF-AT$_c$ antigens typically comprise multiple NF-AT$_c$ antigenic peptides from the same species (e.g., human or mouse), but may comprise a mix of antigenic peptides from NF-AT$_c$ proteins of different species (i.e., an interspecies NF-AT$_c$ polyvalent antigen). Frequently, the spatial order of the antigenic peptide sequences in the primary amino acid sequence of a polyvalent antigen occurs in the same orientation as in the naturally occurring NF-AT$_c$ protein (i.e., a first antigenic peptide sequence that is amino-terminal to a second antigenic peptide sequence in a naturally occurring NF-AT$_c$r protein will be amino-terminal to said second antigenic peptide sequence in a polyvalent antigen. Frequently, spacer peptide sequences will be used to link antigenic peptide sequences in a polyvalent antigen, such spacer peptide sequences may be predetermined, random, or pseudorandom sequences. Spacer peptide sequences may correspond to sequences known to be non-immunogenic to the animal which is to be immunized with the polyvalent antigen, such as a sequence to which the animal has been tolerized. Although many examples of such polyvalent antigens may be given, the following embodiment is provided for illustration and not limitation:
-NAIFLTVSREHERVGC-(aa1)-AKTDRDLCKPNSLVVEIPPFRN-(aa2)-GILKLRNSDIELRKGETD- (SEQ. ID NO:32)

where (aa1) and (aa2) are peptide spacers of at least one amino acid and less than 1000 amino acids; aa1 is a peptide sequence selected independently from the aa2 peptide sequence; the length of aa1 (which may be composed of multiple different amino acids) is independent of the length of aa2 (which may be composed of multiple different amino acids).

Immunogenic NF-AT$_c$ peptides may be used to immunize an animal to raise anti-NF-AT$_c$ antibodies and/or as a source of spleen cells for making a hybridoma library from which to select hybridoma clones which secrete a monoclonal antibody which binds to a NF-AT$_c$ protein with an affinity of $1\times10^7 M^{-1}$ or greater, preferably at least $1\times10^8 M^{-1}$ to $1\times10^9 M^{-1}$. Such immunogenic NF-AT$_c$ peptides can also be used to screen bacteriophage antibody display libraries directly.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel transcription factors or chromatin proteins. Such screening of cDNA expression libraries is well known in the art, and is further described in Young et al., *Proc. Natl. Acad. Sci. U.S.A.* 80:1194–1198 (1983), which is incorporated herein by reference] as well as other published sources. Another use of such antibodies is to identify and/or purify immunocrossreactive proteins that are structurally or evolutionarily related to the native NF-AT$_c$ protein or to the corresponding NF-AT$_c$ fragment (e.g., functional domain; DNA-binding domain) used to generate the antibody. It is believed that such antibodies will find commercial use as such reagents for research applications, just as other antibodies (and biological reagents—such as restriction enzymes and polymerases) are sold commercially.

Various other uses of such antibodies are to diagnose and/or stage leukemias or other immunological disease states, and for therapeutic application (e.g., as cationized antibodies or by targeted liposomal delivery) to treat neoplasia, hyperimmune function, graft rejection, and the like.

NF-AT$_c$ Polynucleotides

Disclosure of the full coding sequence for human NF-AT$_c$ shown in FIG. 1 makes possible the construction of isolated polynucleotides that can direct the expression of NF-AT$_c$, fragments thereof, or analogs thereof. Further, the sequences in FIG. 1 make possible the construction of nucleic acid hybridization probes and PCR primers that can be used to detect RNA and DNA sequences encoding NF-AT$_c$.

Polynucleotides encoding full-length NF-AT$_c$ or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a NF-AT$_c$ polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A preferred NF-AT$_c$ polynucleotide encodes a NF-AT$_c$ polypeptide that comprises at least one of the following amino acids sequences:

-FLRGARREPGARAVF-;
-GAATSPVPPPAAPLPAAAAR-;
-NAIFLTVSREHERVGC-;
-AKTDRDLCKPNSLVVEIPPFRN-
-GILKLRNSDIELRKGETD-;
-LHGYLENEPLMLQLFIGT-;
-EVQPKSHHRAHYETEGSR-.

The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Thus, isolated polynucleotides typically less than approximately 10,000 nucleotides in length and comprising sequences encoding each of the following amino acid sequences:
-FLRGARREPGARAVF-;
-GAATSPVPPPAAPLPAAAAR-;
-NAIFLTVSREHERVGC-;
-AKTDRDLCKPNSLVVEIPPFRN-
-GILKLRNSDIELRKGETD-;
-LHGYLENEPLMLQLFIGT-;
-EVQPKSHHRAHYETEGSR-.
are provided and may be used for, among other uses, the expression of a $NF-AT_c$ polypeptide which can be used as an immunogen, immunological reagent, and the like. Such polynucleotides typically comprise an operably linked promoter for driving expression in a suitable prokaryotic or eukaryotic host cell. One exemplification of such a polynucleotide is the human $NF-AT_c$ cDNA sequence of FIG. 1 cloned in operable linkage to the mammalian expression vector pSRα, many alternative embodiments will be apparent to those of skill in the art, including the use of alternative expression vectors (e.g., pBC12BI and p91023(B); Hanahan J (1983) *J. Mol. Biol.* 166: 577; Cullen et al. (1985) *J. Virol.* 53: 515; Lomedico PT (1982) *Proc. Natl. Acad. Sci. (U.S.A.)* 79: 5798; Morinaga et al. (1984) *Bio/Technology* 2: 636).

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting $NF-AT_c$ RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to the $NF-AT_c$ sequence is retained.

Specific hybridization is defined hereinbefore, and can be roughly summarized as the formation of hybrids between a polynucleotide of the invention (which may include substitutions, deletions, and/or additions) and a specific target polynucleotide such as human $NF-AT_c$ mRNA so that a single band is identified corresponding to each $NF-AT_c$ isoform on a Northern blot of RNA prepared from T cells (i.e., hybridization and washing conditions can be established that permit detection of discrete $NF-AT_c$ mRNA band(s)). Thus, those of ordinary skill in the art can prepare polynucleotides of the invention, which may include substantial additions, deletions, substitutions, or transpositions of nucleotide sequence as compared to sequences shown in FIG. 1 and determine whether specific hybridization is a property of the polynucleotide by performing a Northern blot using RNA prepared from a T lymphocyte cell line which expresses $NF-AT_c$ mRNA and/or by hybridization to a $NF-AT_c$ DNA clone (cDNA or genomic clone).

Specific amplification is defined as the ability of a set of PCR amplimers, when used together in a PCR reaction with a $NF-AT_c$ polynucleotide, to produce substantially a single major amplification product which corresponds to a $NF-AT_c$ gene sequence or mRNA sequence. Generally, human genomic DNA or mRNA from $NF-AT_c$ expressing human cells (e.g., Jurkat cell line) is used as the template DNA sample for the PCR reaction. PCR amplimers that exhibit specific amplification are suitable for quantitative determination of $NF-AT_c$ mRNA by quantitative PCR amplification. $NF-AT_c$ allele-specific amplification products, although having sequence and/or length polymorphisms, are considered to constitute a single amplification product for purposes of this definition.

Generally, hybridization probes comprise approximately at least 25 consecutive nucleotides of a sequence shown in FIG. 1 (for human and murine $NF-AT_c$ detection, respectively), preferably the hybridization probes contain at least 50 consecutive nucleotides of a sequence shown in FIG. 1, and more preferably comprise at least 100 consecutive nucleotides of a sequence shown in FIG. 1. PCR amplimers typically comprise approximately 25 to 50 consecutive nucleotides of a sequence shown in FIG. 1, and usually consist essentially of approximately 25 to 50 consecutive nucleotides of a sequence shown in FIG. 1 with additional nucleotides, if present, generally being at the 5' end so as not to interfere with polymerase-mediated chain extension. PCR amplimer design and hybridization probe selection are well within the scope of discretion of practioners of ordinary skill in the art.

Methods Relating to Genetic Disease

In one preferred embodiment of the invention, hybridization probes that specifically identify the $NF-AT_c$ gene may be used in methods for diagnosing genetic disease. For example, but not for limitation, the genetic disease thus diagnosed may involve a lesion in the relevant $NF-AT_c$ structural or regulatory sequences, or may involve a lesion in a genetic locus closely linked to the $NF-AT_c$ locus and which can be identified by restriction fragment length polymorphism or DNA sequence polymorphism at the linked $NF-AT_c$ locus. In a further preferred embodiment, $NF-AT_c$ gene probes are used to diagnose or identify genetic disease involving predisposition to immunological disease, wherein the amount or functionality of endogenous $NF-AT_c$ is sufficient for the individual to exhibit an increased probability of developing an immune disease, particularly an immune deficiency, arthritis, or autoimmune disease.

Antisense Polynucleotides

Additional embodiments directed to modulation of T cell activation include methods that employ specific antisense polynucleotides complementary to all or part of the sequences shown in FIG. 1. Such complementary antisense polynucleotides may include nucleotide substitutions, additions, deletions, or transpositions, so long as specific hybridization to the relevant target sequence corresponding to FIG. 1 is retained as a functional property of the polynucleotide. Complementary antisense polynucleotides include soluble antisense RNA or DNA oligonucleotides which can hybridize specifically to $NF-AT_c$ mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of NF-AT$_c$ polypeptides. Since NF-AT$_c$ protein expression is associated with T lymphocyte activation, antisense polynucleotides that prevent transcription and/or translation of mRNA corresponding to NF-AT$_c$ polypeptides may inhibit T cell activation and/or reverse the activated phenotype of T cells. Compositions containing a therapeutically effective dosage of NF-AT$_c$ antisense polynucleotides may be administered for treatment of immune diseases, including lymphocytic leukemias, and for inhibition of transplant rejection reactions, if desired. Antisense polynucleotides of various lengths may be produced, although such antisense polynucleotides typically comprise a sequence of about at least 25 consecutive nucleotides which are substantially identical to a naturally-occurring NF-AT$_c$ polynucleotide sequence, and typically which are identical to a sequence shown in FIG. 1.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Isolation of the Cognate Human NF-AT$_c$ Gene

The human homolog of the NF-AT$_c$ cDNA is identified and isolated by screening a human genomic clone library, such as a human genomic library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 1. Typically, hybridization and washing conditions are performed at high stringency according to conventional hybridization procedures. Positive clones are isolated and sequenced. For illustration and not for limitation, a full-length polynucleotide corresponding to the sequence of FIG. 1 may be labeled and used as a hybridization probe to isolate genomic clones from a human or murine genomic clone libary in λEMBL4 or λGEM11 (Promega Corporation, Madison, Wisconsin); typical hybridization conditions for screening plaque lifts (Benton and Davis (1978) *Science* 196: 180) can be: 50% formamide, 5×SSC or SSPE, 1–5× Denhardt's solution, 0.1–1% SDS, 100–200 μg sheared heterologous DNA or tRNA, 0–10% dextran sulfate, 1×10$^5$ to 1×10$^7$ cpm/ml of denatured probe with a specific activity of about 1×108 cpm/μg, and incubation at 42° C. for about 6–36 hours. Prehybridization conditions are essentially identical except that probe is not included and incubation time is typically reduced. Washing conditions are typically 1–3× SSC, 0.1–1% SDS, 50°–70° C. with change of wash solution at about 5–30 minutes.

Nonhuman NF-AT$_c$ cDNAs and genomic clones (i.e., cognate nonhuman NF-AT$_c$ genes) can be analogously isolated from various nonhuman CDNA and genomic clone libraries available in the art (e.g., Clontech, Palo Alto, Calif.) by using probes based on the sequences shown in FIG. 1, with hybridization and washing conditions typically being less stringent than for isolation of human NF-AT$_c$ clones.

Polynucleotides comprising sequences of approximately at least 30–50 nucleotides, preferably at least 100 nucleotides, corresponding to or complementary to the nucleotide sequences shown in FIG. 1 can serve as PCR primers and/or hybridization probes for identifying and isolating germline genes corresponding to NF-AT$_c$. These germline genes may be human or may be from a related mammalian species, preferably rodents or primates. Such germline genes may be -isolated by various methods conventional in the art, including, but not limited to, by hybridization screening of genomic libraries in bacteriophage λ or cosmid libraries, or by PCR amplification of genomic sequences using primers derived from the sequences shown in FIG. 1. Human genomic libraries are publicly available or may be constructed de novo from human DNA.

Genomic clones of NF-AT$_c$, particularly of the murine cognate NF-AT$_c$ gene, may be used to construct homologous targeting constructs for generating cells and transgenic nonhuman animals having at least one functionally disrupted NF-AT$_c$ allele, preferably homozygous for knocked out NF-AT$_c$ alleles. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated NF-AT$_c$ allele. Such mice may be sold commercially as research animals for investigation of immune system development, neoplasia, T cell activation, signal transduction, drug screening, and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a NF-AT$_c$ cDNA or genomic gene copy may be used to construct transgenes for expressing NF-AT$_c$ polypeptides at high levels and/or under the transcriptional control of transcription control sequences which do not naturally occur adjacent to the NF-AT$_c$ gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a NF-AT$_c$-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential immunomodulatory agents, as overexpression of NF-AT$_c$ or inappropriate expression of NF-AT$_c$ may result in a hyperimmune state or enhance graft rejection reactions.

Identification and Isolation of Proteins That Bind NF-AT$_c$

Proteins that bind to NF-AT$_c$ and/or a NFAT-DNA complex are potentially important transcriptional regulatory proteins. Such proteins may be targets for novel immunomodulatory agents. These proteins are referred to herein as accessory proteins. Accessory proteins may be isolated by various methods known in the art.

One preferred method of isolating accessory proteins is by contacting a NF-AT$_c$ polypeptide to an antibody that binds the NF-AT$_c$ polypeptide, and isolating resultant immune complexes. These immune complexes may contain accessory proteins bound to the NF-AT$_c$ polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to NF-AT$_c$ and/or a NFAT-DNA complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a CDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a NF-AT$_c$ polypeptide may be constructed by oligonucleotide synthesis, placed in an expression vector, and expressed in a host cell.

Putative accessory proteins that bind NF-AT$_c$ and/or NFAT-DNA complex in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a NF-AT$_c$ polypeptide. For a general discussion of crosslinking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the NF-AT$_c$ polypeptide. Isolation of crosslinked complexes that include a NF-AT$_c$ polypeptide is preferably accomplished by binding an antibody that binds a NF-AT$_c$ polypeptide with an affinity of at least $1 \times 10^7 M^{-1}$ to a population of crosslinked complexes and recovering only those complexes that bind to the antibody with an affinity of at least $1 \times 10^7 M^{-1}$. Polypeptides that are crosslinked to a NF-AT$_c$ polypeptide are identified as accessory proteins.

Screening assays can be developed for identifying candidate immunomodulatory agents as being agents which inhibit binding of NF-AT$_c$ to an accessory protein (e.g. AP-1) under suitable binding conditions.

Expression of NF-AT$_c$r Polypeptides

The nucleic acid sequences of the present invention capable of ultimately expressing the desired NF-AT$_c$ polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986)

Immunol. Rev. 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a NF-$AT_c$ polypeptide) can be transferred into the host cell by well-known methods, which vary depending on the type of cellular host. For example, CaCl transfection is commonly utilized for prokaryotic cells, whereas $CaPO_4$ treatment or electroporation may be used for other cellular hosts. (See, generally, Maniatis, et al., *Molecular Cloning: A Laboratory Manual*, Cold Spring Harbor Press, (1982), which is incorporated herein by reference). Usually, vectors are episomes and are maintained extrachromosomally.

Expression of recombinant NF-$AT_c$ protein in cells, particularly cells of the lymphopoietic lineage, may be used to identify and isolate genes that are transcriptionally modulated, either positively or negatively, by the presence of NF-$AT_c$ protein. Such genes are typically initially identified as cDNA clones isolated from subtractive cDNA libraries, wherein RNA isolated from cells expressing recombinant NF-$AT_c$ and RNA isolated from control cells (i.e., not expressing recombinant NF-$AT_c$) are used to generate the subtractive libraries and screening probes. In such a manner, NF-$AT_c$-dependent genes may be isolated. NFAT-dependent genes (or their regulatory sequences operably linked to a reporter gene) may be used as a component of an in vitro transcription assay employing a NF-$AT_c$ polypeptide as a necessary component for efficient transcription; such transcription assays may be used to screen for agents which inhibit NF-$AT_c$-dependent gene transcription and are thereby identified as candidate immunomodulatory agents.

Methods for Forensic Identification

The NF-$AT_c$ polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the NF-$AT_c$ gene region. On the basis of the NF-$AT_c$ gene structure, the individual from which the sample originated will be identified with respect to his/her NF-$AT_c$ genotype. The NF-$AT_c$ genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1992 catalog). Corresponding digestion products from each individual are loaded separately on an electrophoretic gel (typically agarose), electrophoresed, blotted to a membrane by Southern blotting, and hybridized with a labeled NF-$AT_c$ probe (e.g., a full-length human NF-$AT_c$ cDNA sequence of FIG. 1). Restriction fragments (bands) which are polymorphic among members of the population are used as a basis to discriminate NF-$AT_c$ genotypes and thereby classify individuals on the basis of their NF-$AT_c$ genotype.

Similar categorization of NF-$AT_c$ genotypes may be performed by sequencing PCR amplification products from a population of individuals and using sequence polymorphisms to identify alleles (genotypes), and thereby identify or classify individuals.

Yeast Two-Hybrid Screening Assays

Yeast two-hybrid systems may be used to screen a mammalian (typically human) cDNA expression library, wherein cDNA is fused to a GAL4 DNA binding domain or activator domain, and a NF-$AT_c$ polypeptide sequence is fused to a GAL4 activator domain or DNA binding domain, respectively. Such a yeast two-hybrid system can screen for cDNAs encoding proteins which bind to NF-$AT_c$ sequences. For example, a cDNA library can be produced from mRNA from a human mature T cell line or other suitable cell type. Such a cDNA library cloned in a yeast two-hybrid expression system (Chien et al. (1991) *Proc. Natl. Acad. Sci. (U.S.A.)* 88: 9578 or *Cell* 72: 233) can be used to identify cDNAs which encode proteins that interact with NF-$AT_c$ and thereby produce expression of the GAL4-dependent reporter gene. Polypeptides which interact with NF-$AT_c$ can also be identified by immunoprecipitation of NF-$AT_c$ with antibody and identification of co-precipitating species. Further, polypeptides that bind NF-$AT_c$ can be identified by screening a peptide library (e.g., a bacteriophage peptide display library, a spatially defined VLSIPS peptide array, and the like) with a NF-$AT_c$ polypeptide.

Methods for Rational Drug Design

NF-$AT_c$ polypeptides, especially those portions which form direct contacts in NF-AT complexes, can be used for rational drug design of candidate NFAT-modulating agents (e.g., antineoplastics and immunomodulators). The substantially purified NF-$AT_c$ and the identification of NF-$AT_c$ as a docking partner for AP-1 activities as provided herein permits production of substantially pure NFAT polypeptide complexes and computational models which can be used for protein X-ray crystallography or other structure analysis methods, such as the DOCK program (Kuntz et al. (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a NF-ATC polypeptide: AP-1 polypeptide complex. Thus, the present invention may be used to design drugs, including drugs with a capacity to inhibit binding of NF-$AT_c$ to form NFAT.

The following examples are offered by way of example and not by way of limitation. Variations and alternate embodiments will be apparent to those of skill in the art.

EXPERIMENTAL EXAMPLES

Example 1

Determination of the nucleotide and amino acid sequence of human NF-$AT_c$ cDNA

This example represents the isolation and purification of this novel human NF-AT protein, NF-$AT_c$, the determination of the amino acid sequence of its fragments and the isolation and sequencing of the cDNA clone encoding this protein.

The protein was purified from bovine thymus glands obtained from newborn calves. Approximately 20 bovine thymuses were homogenized to make a cytosolic extract which was then subjected sequentially to 1) ammonium sulfate precipitation, 2) sulphopropyl Sepharose chromatography, 3) heparin agarose chromatography, 4) affinity chromatography using a multimerized binding site for NF-AT, with the sequence 5'-ACGCCCAAAGAGGAAAATTTGTTTCATACA-3' coupled to sepharose CL4B, and 5) HPLC on a reverse phase C4 column. The resulting purified protein was subjected to cleavage with LysC/ArgC and fragments isolated by HPLC. The sequences of these individual fragments were then determined by automated Edman degradation. Sequences obtained included: LRNSDIELRKGETDIGR (SEQ. ID NO:34) and LRNADIELR(SEQ. ID NO:35). Degenerate oligos corresponding to GETDIG (SEQ. ID NO:36) (reverse primer) and RNADIE (SEQ. ID NO:37) (forward primer) were made. The degenerate oligo PCR primers had the following sequences:

A forward: (A/C)GIAA(C/T)GCIGA(C/T)AT(A/C/T)GA (A/G) (SEQ. ID NO:38)

A reverse: ICC(A/G/T)AT(A/G)TCIGT(C/T)TCICC (SEQ. ID NO:39)

To isolate the cDNA, oligonucleotide probes were made corresponding to the determined amino acid sequence and used as PCR primers to isolate a 45 base fragment from bovine cDNA prepared from the bovine thymus. The bovine PCR product comprised the nucleotide sequence CTG CGG AAA which encodes -L-R-K-. The same 45 bp fragment can be amplified from human and mouse sources.

This bovine PCR product was then used to screen a cDNA library of the human Jurkat T cell line. Clones were isolated at frequencies of about 1 in 100,000 to 1 in 200,000. A total of five human cDNA clones of various lengths were isolated. Two overlapping clones, one containing the 5' end and one containing the 3' end were ligated together using a unique EcoRI restriction site present in each clone, to produce a full-length cDNA which corresponded in length to the messenger RNA determined by Northern blotting.

The sequence of the NF-AT$_c$ cDNA was determined by the Sanger method and the complete nucleotide and predicted amino acid sequence is shown in FIG. 1. The initiator methionine indicated in FIG. 1 (boldface, indicated) was determined by fusing this reading frame to a glutathione transferase gene and transfecting the resultant clone into bacteria. The resultant clone produced a fusion protein of the proper molecular weight, indicating that the reading frame designated with the initiator methionine is indeed the correct reading frame. The position of the stop codon was determined by a similar procedure. In addition, the stop codon corresponds to the reading frame for nine of the determined amino acid sequences.

Example 2

Expression of NF-AT$_c$ in T and non-T cells The cDNA shown in FIG.__ was fused to the Hemophilus influenza hemagalutinin (HA) 12 amino acid epitope tag in the determined reading frame and operably linked to the SRα promoter in the vector pBJ5 (Lin et al, 1990, Science 249:677–679). The resultant construct was transiently transfected by electroporation into Jurkat human T lymphocytes, and into Cos fibroblast cells. Expression of the epitope-tagged NF-AT$_c$ protein was determined by Western blotting of whole cell extracts prepared from the transfected cells, using an antibody (12CA5, Berkeley Antibody Co., Calif.) that detects the HA epitope.

FIG. 2 shows that NF-AT$_c$ cDNA construct is able to express a protein of approximately 120 kDA corresponding precisely in size to that of the purified protein, in both Jurkat T cells and Cos cells (see lanes 3 and 6 labeled NF-AT*. Lane 2 shows as control, NF-AT without the epitope tag which cannot be detected in the Western blot).

Example 3

Transfection of NF-AT$_c$ activates transcription in both Cos and Jurkat cells The NF-AT$_c$ cDNA was operably linked to a portion of the SV40 early gene promoter and the HIV transcription regulatory regions in the pBJ vector. This expression vector was co- tranfected into Jurkat and Cos cells with either a) three copies of NF-AT binding site linked to and directing transcription of luciferase (results shown in FIG. 3A and 3B) the entire IL-2 enhancer/promoter directing transcription of luciferase (results shown in FIG. 3B). Cytosolic extracts were prepared and luciferase assays carried out by standard procedures (de Wet et al, 1987, Mol. Cell. Biol. 7:724–837).

Figure 3A:
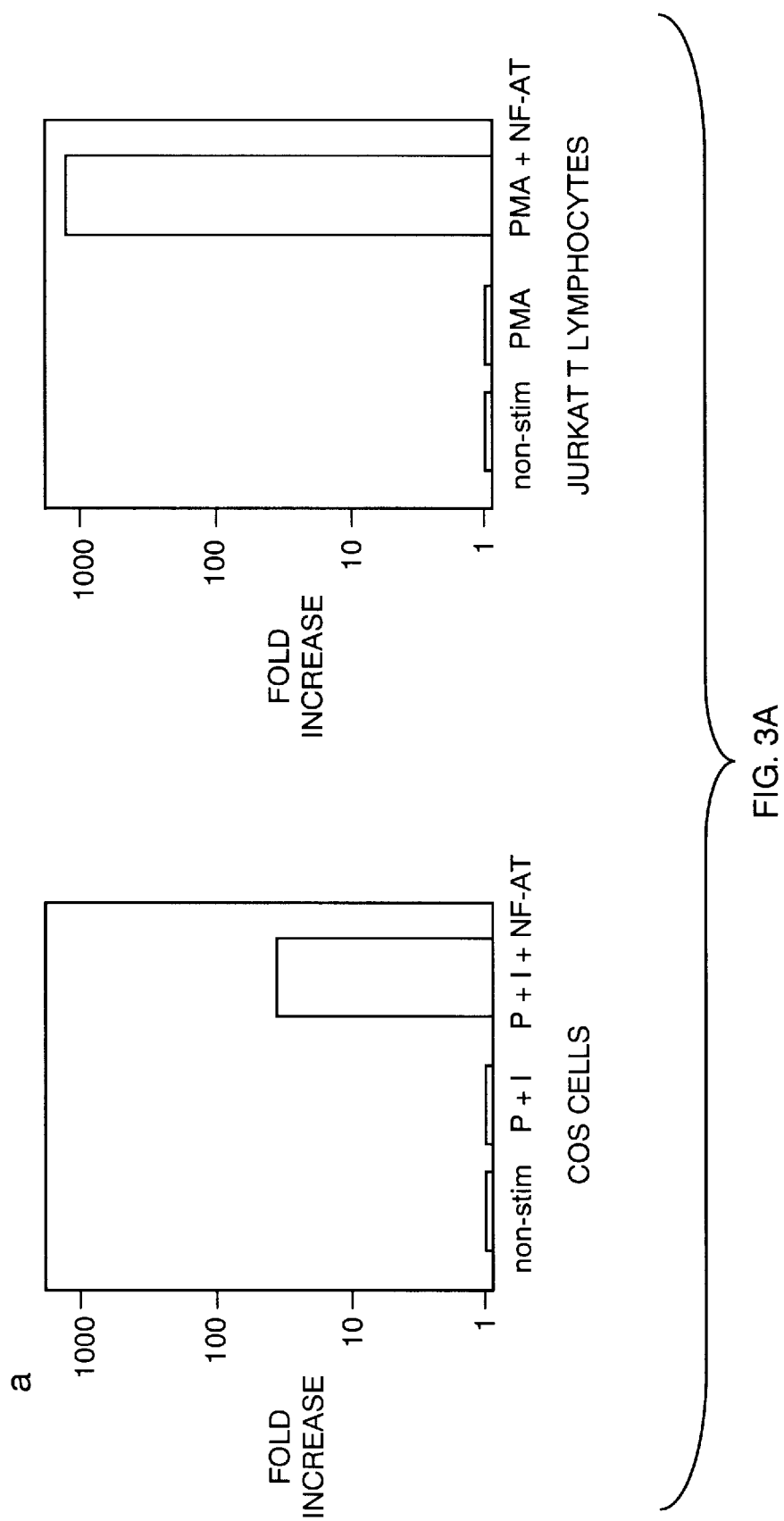
FIG. 3A and 3B show that the NF-AT$_c$ cDNA clone encodes a protein that activates transcription from an NF-AT site and is capable of activating the IL-2 promoter in non-T cells.
Figure 3B:
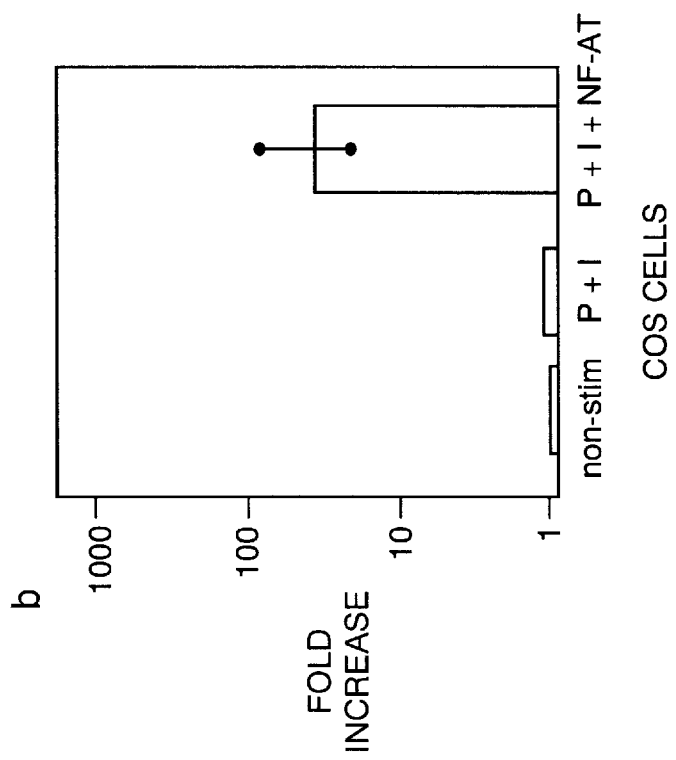

The results demonstrate that in both Cos cells and Jurkat cells, overexpression of the NF-AT$_c$ protein dramatically enhances NF-AT-dependent transcription by 50–1000 fold (see FIG. 3A). In addition, overexpression of the NF-AT$_c$ protein in Cos cells activates the IL-2 promoter, which in the absence of NF-AT$_c$ cannot otherwise be activated (see FIG. 3B).

These results indicate that the cDNA clone encodes a functional NF-AT$_c$ protein and that NF-AT$_c$ is the protein which restricts expression of interleukin-2 to T cells.

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 2749 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

(A) NAME/KEY: CDS
(B) LOCATION: 103..2385

(xi) SEQUENCE DESCRIPTION: SEQ ID NO:1:

```
GAATTCCGCA GGGCGCGGGC ACCGGGGCGC GGGCAGGGCT CGGAGCCACC GCGCAGGTCC         60

TAGGGCCGCG GCGGGCCCCG CCACGCGCGC ACACGCCCCT CG ATG ACT TTC CTC           114
                                               Met Thr Phe Leu
                                               1

CGG GGC GCG CGG CGT GAG CCC GGG GCG AGG GCT GTC TTC CCG GAG ACC         162
Arg Gly Ala Arg Arg Glu Pro Gly Ala Arg Ala Val Phe Pro Glu Thr
    5               10                  15                  20

CGA CCC CGG CAG CGC GGG GCG GCC ACT TCT CCT GTG CCT CCG CCC GCT         210
Arg Pro Arg Gln Arg Gly Ala Ala Thr Ser Pro Val Pro Pro Pro Ala
                25                  30                  35

GCT CCA CTC CCC GCC GCC GCC GCG CGG ATG CCA AGC ACC AGC TTT CCA         258
Ala Pro Leu Pro Ala Ala Ala Ala Arg Met Pro Ser Thr Ser Phe Pro
        40                  45                  50

GTC CCT TCC AAG TTT CCA CTT GGC CCT GCG GCT GCG GTC TTC GGG AGA         306
Val Pro Ser Lys Phe Pro Leu Gly Pro Ala Ala Ala Val Phe Gly Arg
            55                  60                  65

GGA GAA ACT TTG GGG CCC GCG CCG CGC GCC GGC GGC ACC ATG AAG TCA         354
Gly Glu Thr Leu Gly Pro Ala Pro Arg Ala Gly Gly Thr Met Lys Ser
        70                  75                  80

GCG GAG GAA GAA CAC TAT GGC TAT GCA TCC TCC AAC GTC AGC CCC GCC         402
Ala Glu Glu Glu His Tyr Gly Tyr Ala Ser Ser Asn Val Ser Pro Ala
85                  90                  95                  100

CTG CCG CTC CCC ACG GCG CAC TCC ACC CTG CCG GCC CCG TGC CAC AAC         450
Leu Pro Leu Pro Thr Ala His Ser Thr Leu Pro Ala Pro Cys His Asn
                105                 110                 115

CTT CAG ACC TCC ACA CCG GGC ATC ATC CCG CCG GCG GAT CAC CCC TCG         498
Leu Gln Thr Ser Thr Pro Gly Ile Ile Pro Pro Ala Asp His Pro Ser
            120                 125                 130

GGG TAC GGA GCA GCT TTG GAC GGT GGG CCC GCG GGC TAC TTC CTC TCC         546
Gly Tyr Gly Ala Ala Leu Asp Gly Gly Pro Ala Gly Tyr Phe Leu Ser
        135                 140                 145

TCC GGC CAC ACC AGG CCT GAT GGG GCC CCT GCC CTG GAG AGT CCT CGC         594
Ser Gly His Thr Arg Pro Asp Gly Ala Pro Ala Leu Glu Ser Pro Arg
    150                 155                 160

ATC GAG ATA ACC TCG TGC TTG GGC CTG TAC CAC AAC AAT AAC CAG TTT         642
Ile Glu Ile Thr Ser Cys Leu Gly Leu Tyr His Asn Asn Asn Gln Phe
165                 170                 175                 180

TTC CAC GAT GTG GAG GTG GAA GAC GTC CTC CCT AGC TCC AAA CGG TCC         690
Phe His Asp Val Glu Val Glu Asp Val Leu Pro Ser Ser Lys Arg Ser
                185                 190                 195

CCC TCC ACG GCC ACG CTG AGT CTG CCC AGC CTG GAG GCC TAC AGA GAC         738
Pro Ser Thr Ala Thr Leu Ser Leu Pro Ser Leu Glu Ala Tyr Arg Asp
            200                 205                 210

CCC TCG TGC CTG AGC CCG GCC AGC AGC CTG TCC TCC CGG AGC TGC AAC         786
Pro Ser Cys Leu Ser Pro Ala Ser Ser Leu Ser Ser Arg Ser Cys Asn
        215                 220                 225

TCA GAG GCC TCC TCC TAC GAG TCC AAC TAC TCG TAC CCG TAC GCG TCC         834
Ser Glu Ala Ser Ser Tyr Glu Ser Asn Tyr Ser Tyr Pro Tyr Ala Ser
    230                 235                 240

CCC CAG ACG TCG CCA TGG CAG TCT CCC TGC GTG TCT CCC AAG ACC ACG         882
Pro Gln Thr Ser Pro Trp Gln Ser Pro Cys Val Ser Pro Lys Thr Thr
245                 250                 255                 260

GAC CCC GAG GAG GGC TTT CCC CGC GGG CTG GGG GCC TGC ACA CTG CTG         930
Asp Pro Glu Glu Gly Phe Pro Arg Gly Leu Gly Ala Cys Thr Leu Leu
                265                 270                 275

GGT TCC CCG CAG CAC TCC CCC TCC ACC TCG CCC CGC GCC AGC GTC ACT         978
```

-continued

```
                    Gly Ser Pro Gln His Ser Pro Ser Thr Ser Pro Arg Ala Ser Val Thr
                                    280             285             290

GAG GAG AGC TGG CTG GGT GCC CGC TCC TCC AGA CCC GCG TCC CCT TGC          1026
Glu Glu Ser Trp Leu Gly Ala Arg Ser Ser Arg Pro Ala Ser Pro Cys
        295             300             305

AAC AAG AGG AAG TAC AGC CTC AAC GGC CGG CAG CCG CCC TAC TCA CCC          1074
Asn Lys Arg Lys Tyr Ser Leu Asn Gly Arg Gln Pro Pro Tyr Ser Pro
310             315             320

CAC CAC TCG CCC ACG CCG TCC CCG CAC GGC TCC CCG CGG GTC AGC GTG          1122
His His Ser Pro Thr Pro Ser Pro His Gly Ser Pro Arg Val Ser Val
325             330             335             340

ACC GAC GAC TCG TGG TTG GGC AAC ACC ACC CAG TAC ACC AGC TCG GCC          1170
Thr Asp Asp Ser Trp Leu Gly Asn Thr Thr Gln Tyr Thr Ser Ser Ala
                345             350             355

ATC GTG GCC GCC ATC AAC GCG CTG ACC ACC GAC AGC AGC CTG GAC CTG          1218
Ile Val Ala Ala Ile Asn Ala Leu Thr Thr Asp Ser Ser Leu Asp Leu
            360             365             370

GGA GAT GGC GTC CCT GTC AAG TCC CGC AAG ACC ACC CTG GAG CAG CCG          1266
Gly Asp Gly Val Pro Val Lys Ser Arg Lys Thr Thr Leu Glu Gln Pro
        375             380             385

CCC TCA GTG GCG CTC AAG GTG GAG CCC GTC GGG GAG GAC CTG GGC AGC          1314
Pro Ser Val Ala Leu Lys Val Glu Pro Val Gly Glu Asp Leu Gly Ser
    390             395             400

CCC CCG CCC CCG GCC GAC TTC GCG CCC GAA GAC TAC TCC TCT TTC CAG          1362
Pro Pro Pro Pro Ala Asp Phe Ala Pro Glu Asp Tyr Ser Ser Phe Gln
405             410             415             420

CAC ATC AGG AAG GGC GGC TTC TGC GAC CAG TAC CTG GCG GTG CCG CAG          1410
His Ile Arg Lys Gly Gly Phe Cys Asp Gln Tyr Leu Ala Val Pro Gln
                425             430             435

CAC CCC TAC CAG TGG GCG AAG CCC AAG CCC CTG TCC CCT ACG TCC TAC          1458
His Pro Tyr Gln Trp Ala Lys Pro Lys Pro Leu Ser Pro Thr Ser Tyr
            440             445             450

ATG AGC CCG ACC CTG CCC GCC CTG GAC TGG CAG CTG CCG TCC CAC TCA          1506
Met Ser Pro Thr Leu Pro Ala Leu Asp Trp Gln Leu Pro Ser His Ser
        455             460             465

GGC CCG TAT GAG CTT CGG ATT GAG GTG CAG CCC AAG TCC CAC CAC CGA          1554
Gly Pro Tyr Glu Leu Arg Ile Glu Val Gln Pro Lys Ser His His Arg
    470             475             480

GCC CAC TAC GAG ACG GAG GGC AGC CGG GGG GCC GTG AAG GCG TCG GCC          1602
Ala His Tyr Glu Thr Glu Gly Ser Arg Gly Ala Val Lys Ala Ser Ala
485             490             495             500

GGA GGA CAC CCC ATC GTG CAG CTG CAT GGC TAC TTG GAG AAT GAG CCG          1650
Gly Gly His Pro Ile Val Gln Leu His Gly Tyr Leu Glu Asn Glu Pro
                505             510             515

CTG ATG CTG CAG CTT TTC ATT GGG ACG GCG GAC GAC CGC CTG CTG CGC          1698
Leu Met Leu Gln Leu Phe Ile Gly Thr Ala Asp Asp Arg Leu Leu Arg
            520             525             530

CCG CAC GCC TTC TAC CAG GTG CAC CGC ATC ACA GGG AAG ACC GTG TCC          1746
Pro His Ala Phe Tyr Gln Val His Arg Ile Thr Gly Lys Thr Val Ser
        535             540             545

ACC ACC AGC CAC GAG GCT ATC CTC TCC AAC ACC AAA GTC CTG GAG ATC          1794
Thr Thr Ser His Glu Ala Ile Leu Ser Asn Thr Lys Val Leu Glu Ile
    550             555             560

CCA CTC CTG CCG GAG AAC AGC ATG CGA GCC GTC ATT GAC TGT GCC GGA          1842
Pro Leu Leu Pro Glu Asn Ser Met Arg Ala Val Ile Asp Cys Ala Gly
565             570             575             580

ATC CTG AAA CTC AGA AAC TCC GAC ATT GAA CTT CGG AAA GGA GAG ACG          1890
Ile Leu Lys Leu Arg Asn Ser Asp Ile Glu Leu Arg Lys Gly Glu Thr
                585             590             595

GAC ATC GGG AGG AAG AAC ACA CGG GTA CGG CTG GTG TTC CGC GTT CAC          1938
```

| | | | | | | | | | | | | | | | |
|---|---|---|---|---|---|---|---|---|---|---|---|---|---|---|---|
|Asp|Ile|Gly|Arg|Lys|Asn|Thr|Arg|Val|Arg|Leu|Val|Phe|Arg|Val|His|
| | | |600| | | |605| | | | |610| | | |

```
GTC  CCG  CAA  CCC  AGC  GGC  CGC  ACG  CTG  TCC  CTG  CAG  GTG  GCC  TCC  AAC      1986
Val  Pro  Gln  Pro  Ser  Gly  Arg  Thr  Leu  Ser  Leu  Gln  Val  Ala  Ser  Asn
          615                      620                      625

CCC  ATC  GAA  TGC  TCC  CAG  CGC  TCA  GCT  CAG  GAG  CTG  CCT  CTG  GTG  GAG      2034
Pro  Ile  Glu  Cys  Ser  Gln  Arg  Ser  Ala  Gln  Glu  Leu  Pro  Leu  Val  Glu
          630                      635                      640

AAG  CAG  AGC  ACG  GAC  AGC  TAT  CCG  GTC  GTG  GGC  GGG  AAG  AAG  ATG  GTC      2082
Lys  Gln  Ser  Thr  Asp  Ser  Tyr  Pro  Val  Val  Gly  Gly  Lys  Lys  Met  Val
645                      650                      655                      660

CTG  TCT  GGC  CAC  AAC  TTC  CTG  CAG  GAC  TCC  AAG  GTC  ATT  TTC  GTG  GAG      2130
Leu  Ser  Gly  His  Asn  Phe  Leu  Gln  Asp  Ser  Lys  Val  Ile  Phe  Val  Glu
               665                      670                      675

AAA  GCC  CCA  GAT  GGC  CAC  CAT  GTC  TGG  GAG  ATG  GAA  GCG  AAA  ACT  GAC      2178
Lys  Ala  Pro  Asp  Gly  His  His  Val  Trp  Glu  Met  Glu  Ala  Lys  Thr  Asp
               680                      685                      690

CGG  GAC  CTG  TGC  AAG  CCG  AAT  TCT  CTG  GTG  GTT  GAG  ATC  CCG  CCA  TTT      2226
Arg  Asp  Leu  Cys  Lys  Pro  Asn  Ser  Leu  Val  Val  Glu  Ile  Pro  Pro  Phe
          695                      700                      705

CGG  AAT  CAG  AGG  ATA  ACC  AGC  CCC  GTT  CAC  GTC  AGT  TTC  TAC  GTC  TGC      2274
Arg  Asn  Gln  Arg  Ile  Thr  Ser  Pro  Val  His  Val  Ser  Phe  Tyr  Val  Cys
     710                      715                      720

AAC  GGG  AAG  AGA  AAG  CGA  AGC  CAG  TAC  CAG  CGT  TTC  ACC  TAC  CTT  CCC      2322
Asn  Gly  Lys  Arg  Lys  Arg  Ser  Gln  Tyr  Gln  Arg  Phe  Thr  Tyr  Leu  Pro
725                      730                      735                      740

GCC  AAC  GGT  AAC  GCC  ATC  TTT  CTA  ACC  GTA  AGC  CGT  GAA  CAT  GAG  CGC      2370
Ala  Asn  Gly  Asn  Ala  Ile  Phe  Leu  Thr  Val  Ser  Arg  Glu  His  Glu  Arg
               745                      750                      755

GTG  GGG  TGC  TTT  TTC  TAAAGACGCA  GAAACGACGT  CGCCGTAAAG  CAGCGTGGCG            2425
Val  Gly  Cys  Phe  Phe
               760

TGTTGCACAT  TTAACTGTGT  GATGTCCCGT  TAGTGAGACC  GAGCCATCGA  TGCCCTGAAA            2485

AGGAAAGGAA  AAGGGAAGCT  TCGGATGCAT  TTTCCTTGAT  CCCTGTTGGG  GGTGGGGGGC            2545

GGGGGTTGCA  TACTCAGATA  GTCACGGTTA  TTTTGCTTCT  TGCGAATGTA  AACAGCCAA             2605

GGGGAAAACA  TGGCTCTTCT  GCTCCAAAAA  ACTGAGGGGG  TCCTGGTGTG  CATTTGCACC            2665

CTAAAGCTGC  TTACGGTGAA  AAGGCAAATA  GGTATAGCTA  TTTTGCAGGC  ACCTTTAGGA            2725

ATAAACTTTG  CTTTTAAAAA  AAAA                                                      2749
```

( 2 ) INFORMATION FOR SEQ ID NO:2:

( i ) SEQUENCE CHARACTERISTICS:
        ( A ) LENGTH: 761 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Phe  Leu  Arg  Gly  Ala  Arg  Arg  Glu  Pro  Gly  Ala  Arg  Ala  Val
1                   5                        10                       15

Phe  Pro  Glu  Thr  Arg  Pro  Arg  Gln  Arg  Gly  Ala  Ala  Thr  Ser  Pro  Val
               20                  25                       30

Pro  Pro  Pro  Ala  Ala  Pro  Leu  Pro  Ala  Ala  Ala  Ala  Arg  Met  Pro  Ser
          35                  40                       45

Thr  Ser  Phe  Pro  Val  Pro  Ser  Lys  Phe  Pro  Leu  Gly  Pro  Ala  Ala  Ala
     50                  55                       60

Val  Phe  Gly  Arg  Gly  Glu  Thr  Leu  Gly  Pro  Ala  Pro  Arg  Ala  Gly  Gly
```

-continued

```
                65                                  70                                  75                                  80
Thr   Met   Lys   Ser   Ala   Glu   Glu   Glu   His   Tyr   Gly   Tyr   Ala   Ser   Ser   Asn
                        85                              90                              95
Val   Ser   Pro   Ala   Leu   Pro   Leu   Pro   Thr   Ala   His   Ser   Thr   Leu   Pro   Ala
                        100                             105                             110
Pro   Cys   His   Asn   Leu   Gln   Thr   Ser   Thr   Pro   Gly   Ile   Ile   Pro   Pro   Ala
                        115                             120                             125
Asp   His   Pro   Ser   Gly   Tyr   Gly   Ala   Ala   Leu   Asp   Gly   Gly   Pro   Ala   Gly
            130                           135                             140
Tyr   Phe   Leu   Ser   Ser   Gly   His   Thr   Arg   Pro   Asp   Gly   Ala   Pro   Ala   Leu
145                                 150                           155                           160
Glu   Ser   Pro   Arg   Ile   Glu   Ile   Thr   Ser   Cys   Leu   Gly   Leu   Tyr   His   Asn
                              165                     170                           175
Asn   Asn   Gln   Phe   Phe   His   Asp   Val   Glu   Val   Glu   Asp   Val   Leu   Pro   Ser
                        180                           185                           190
Ser   Lys   Arg   Ser   Pro   Ser   Thr   Ala   Thr   Leu   Ser   Leu   Pro   Ser   Leu   Glu
                  195                           200                           205
Ala   Tyr   Arg   Asp   Pro   Ser   Cys   Leu   Ser   Pro   Ala   Ser   Ser   Leu   Ser   Ser
            210                           215                           220
Arg   Ser   Cys   Asn   Ser   Glu   Ala   Ser   Ser   Tyr   Glu   Ser   Asn   Tyr   Ser   Tyr
225                           230                           235                           240
Pro   Tyr   Ala   Ser   Pro   Gln   Thr   Ser   Pro   Trp   Gln   Ser   Pro   Cys   Val   Ser
                        245                           250                           255
Pro   Lys   Thr   Thr   Asp   Pro   Glu   Glu   Gly   Phe   Pro   Arg   Gly   Leu   Gly   Ala
                  260                           265                           270
Cys   Thr   Leu   Leu   Gly   Ser   Pro   Gln   His   Ser   Pro   Ser   Thr   Ser   Pro   Arg
            275                           280                           285
Ala   Ser   Val   Thr   Glu   Glu   Ser   Trp   Leu   Gly   Ala   Arg   Ser   Ser   Arg   Pro
290                           295                           300
Ala   Ser   Pro   Cys   Asn   Lys   Arg   Lys   Tyr   Ser   Leu   Asn   Gly   Arg   Gln   Pro
305                           310                           315                           320
Pro   Tyr   Ser   Pro   His   His   Ser   Pro   Thr   Pro   Ser   Pro   His   Gly   Ser   Pro
                        325                           330                           335
Arg   Val   Ser   Val   Thr   Asp   Asp   Ser   Trp   Leu   Gly   Asn   Thr   Thr   Gln   Tyr
                  340                           345                           350
Thr   Ser   Ser   Ala   Ile   Val   Ala   Ala   Ile   Asn   Ala   Leu   Thr   Thr   Asp   Ser
            355                           360                           365
Ser   Leu   Asp   Leu   Gly   Asp   Gly   Val   Pro   Val   Lys   Ser   Arg   Lys   Thr   Thr
      370                           375                           380
Leu   Glu   Gln   Pro   Pro   Ser   Val   Ala   Leu   Lys   Val   Glu   Pro   Val   Gly   Glu
385                           390                           395                           400
Asp   Leu   Gly   Ser   Pro   Pro   Pro   Ala   Asp   Phe   Ala   Pro   Glu   Asp   Tyr
                        405                           410                           415
Ser   Ser   Phe   Gln   His   Ile   Arg   Lys   Gly   Gly   Phe   Cys   Asp   Gln   Tyr   Leu
                  420                           425                           430
Ala   Val   Pro   Gln   His   Pro   Tyr   Gln   Trp   Ala   Lys   Pro   Lys   Pro   Leu   Ser
                  435                           440                           445
Pro   Thr   Ser   Tyr   Met   Ser   Pro   Thr   Leu   Pro   Ala   Leu   Asp   Trp   Gln   Leu
            450                           455                           460
Pro   Ser   His   Ser   Gly   Pro   Tyr   Glu   Leu   Arg   Ile   Glu   Val   Gln   Pro   Lys
465                           470                           475                           480
Ser   His   His   Arg   Ala   His   Tyr   Glu   Thr   Glu   Gly   Ser   Arg   Gly   Ala   Val
                        485                           490                           495
```

| | | | | | | | | | | | | | |
|---|---|---|---|---|---|---|---|---|---|---|---|---|---|
| Lys | Ala | Ser | Ala<br>500 | Gly | Gly | His | Pro | Ile<br>505 | Val | Gln | Leu | His | Gly<br>510 | Tyr | Leu |
| Glu | Asn | Glu<br>515 | Pro | Leu | Met | Leu | Gln<br>520 | Leu | Phe | Ile | Gly | Thr<br>525 | Ala | Asp | Asp |
| Arg | Leu<br>530 | Leu | Arg | Pro | His | Ala<br>535 | Phe | Tyr | Gln | Val | His<br>540 | Arg | Ile | Thr | Gly |
| Lys<br>545 | Thr | Val | Ser | Thr | Thr<br>550 | Ser | His | Glu | Ala | Ile<br>555 | Leu | Ser | Asn | Thr | Lys<br>560 |
| Val | Leu | Glu | Ile | Pro<br>565 | Leu | Leu | Pro | Glu | Asn<br>570 | Ser | Met | Arg | Ala | Val<br>575 | Ile |
| Asp | Cys | Ala | Gly<br>580 | Ile | Leu | Lys | Leu | Arg<br>585 | Asn | Ser | Asp | Ile | Glu<br>590 | Leu | Arg |
| Lys | Gly | Glu<br>595 | Thr | Asp | Ile | Gly | Arg<br>600 | Lys | Asn | Thr | Arg | Val<br>605 | Arg | Leu | Val |
| Phe | Arg<br>610 | Val | His | Val | Pro | Gln<br>615 | Pro | Ser | Gly | Arg | Thr<br>620 | Leu | Ser | Leu | Gln |
| Val<br>625 | Ala | Ser | Asn | Pro | Ile<br>630 | Glu | Cys | Ser | Gln | Arg<br>635 | Ser | Ala | Gln | Glu | Leu<br>640 |
| Pro | Leu | Val | Glu | Lys<br>645 | Gln | Ser | Thr | Asp | Ser<br>650 | Tyr | Pro | Val | Val | Gly<br>655 | Gly |
| Lys | Lys | Met | Val<br>660 | Leu | Ser | Gly | His | Asn<br>665 | Phe | Leu | Gln | Asp | Ser<br>670 | Lys | Val |
| Ile | Phe | Val<br>675 | Glu | Lys | Ala | Pro | Asp<br>680 | Gly | His | His | Val | Trp<br>685 | Glu | Met | Glu |
| Ala | Lys<br>690 | Thr | Asp | Arg | Asp | Leu<br>695 | Cys | Lys | Pro | Asn | Ser<br>700 | Leu | Val | Val | Glu |
| Ile<br>705 | Pro | Pro | Phe | Arg | Asn<br>710 | Gln | Arg | Ile | Thr | Ser<br>715 | Pro | Val | His | Val | Ser<br>720 |
| Phe | Tyr | Val | Cys | Asn<br>725 | Gly | Lys | Arg | Lys | Arg<br>730 | Ser | Gln | Tyr | Gln | Arg<br>735 | Phe |
| Thr | Tyr | Leu | Pro<br>740 | Ala | Asn | Gly | Asn | Ala<br>745 | Ile | Phe | Leu | Thr | Val<br>750 | Ser | Arg |
| Glu | His | Glu<br>755 | Arg | Val | Gly | Cys | Phe<br>760 | Phe | | | | | | | |

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTCCTCCGGG GCGCGCGGCG TGAGCCCGGG GCGAGG    36

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAGCGCGGGG CGGCCACTTC TCCTGTGCCT CCGCCCGCTG CT    42

( 2 ) INFORMATION FOR SEQ ID NO:5:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GCCGCGCGGA TGCCAAGCAC CAGCTTTCCA GTCCCTTCCA AG  42

( 2 ) INFORMATION FOR SEQ ID NO:6:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CCAACGTCAG CCCCGCCCTG CCGCTCCCCA CGGCGCACTC CA  42

( 2 ) INFORMATION FOR SEQ ID NO:7:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

TTCAGACCTC CACACCGGGC ATCATCCCGC CGGCGG  36

( 2 ) INFORMATION FOR SEQ ID NO:8:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

GCCACACCAG GCCTGATGGG GCCCCTGCCC TGGAGAGTCC TC  42

( 2 ) INFORMATION FOR SEQ ID NO:9:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

AGTCTGCCCA GCCTGGAGGC CTACAGAGAC CCCTCGTGCC TG  42

( 2 ) INFORMATION FOR SEQ ID NO:10:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

GTGTCTCCCA AGACCACGGA CCCCGAGGAG GGCTTTCCC  39

( 2 ) INFORMATION FOR SEQ ID NO:11:

( i ) SEQUENCE CHARACTERISTICS:
    ( A ) LENGTH: 42 base pairs (B) TYPE: nucleic acid
(C) STRANDEDNESS: single
(D) TOPOLOGY: linear (xi) SEQUENCE DESCRIPTION: SEQ ID NO:11:

AGCTGGCTGG GTGCCCGCTC CTCCAGACCC GCGTCCCTT GC 42

(2) INFORMATION FOR SEQ ID NO:12:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:12:

TACAGCCTCA ACGGCCGGCA GCCGCCCTAC TCACCCCACC AC 42

(2) INFORMATION FOR SEQ ID NO:13:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:13:

GACCACCGAC AGCAGCCTGG ACCTGGGAGA TGGCGTCCCT GT 42

(2) INFORMATION FOR SEQ ID NO:14:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:14:

CCTGGGCAGC CCCCGCCCC CGGCCGACTT CGCGCCCGAA GA 42

(2) INFORMATION FOR SEQ ID NO:15:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:15:

GCTCCCCTAC CAGTGGCGAA GCCCAAGCCC CTGTCCCCTA CG 42

(2) INFORMATION FOR SEQ ID NO:16:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:16:

CTTCGGATTG AGGTGCAGCC CAAGTCCCAC CACCGAGCCC AC 42

(2) INFORMATION FOR SEQ ID NO:17:

(i) SEQUENCE CHARACTERISTICS:
(A) LENGTH: 42 base pairs
(B) TYPE: nucleic acid
(C) STRANDEDNESS: single ( D ) TOPOLOGY: linear ( x i ) SEQUENCE DESCRIPTION: SEQ ID NO:17:

CATGGCTACT TGGAGAATGA GCCGCTGATG CTGCAGCTTT TC 42

( 2 ) INFORMATION FOR SEQ ID NO:18:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AAGACCGTGT CCACCACCAG CCACGAGGCT ATCCTCTCCA AC 42

( 2 ) INFORMATION FOR SEQ ID NO:19:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TCAGCTCAGG AGCTGCCTCT GGTGGAGAAG CAGAGCACGG AC 42

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

AACGCCATCT TTCTAACCGT AAGCCGTGAA CATGAGCGCG 40

( 2 ) INFORMATION FOR SEQ ID NO:21:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

AGAAACGACG TCGCCGTAAA GCAGCGTGGC GTGTGGCA 38

( 2 ) INFORMATION FOR SEQ ID NO:22:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCATACTCAG ATAGTCACGG TTATTTTGCT TCTTGCGAAT G 41

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear -continued (xi) SEQUENCE DESCRIPTION: SEQ ID NO:23:

AGGGCGCGGG CACCGGGGCG CGGGCAGGGC TCGGAG                        36

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:24:

GCAAGAAGCA AAATAACCGT GACTATCTGA GTATGC                        36

(2) INFORMATION FOR SEQ ID NO:25:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:25:

Phe Leu Arg Gly Ala Arg Arg Glu Pro Gly Ala Arg Ala Val Phe
1               5                   10                  15

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:26:

Gly Ala Ala Thr Ser Pro Val Pro Pro Pro Ala Ala Pro Leu Pro Ala
1               5                   10                  15
Ala Ala Ala Arg
            20

(2) INFORMATION FOR SEQ ID NO:27:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:27:

Asn Ala Ile Phe Leu Thr Val Ser Arg Glu His Glu Arg Val Gly Cys
1               5                   10                  15

(2) INFORMATION FOR SEQ ID NO:28:

(i) SEQUENCE CHARACTERISTICS:
        (A) LENGTH: 22 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:28:

Ala Lys Thr Asp Arg Asp Leu Cys Lys Pro Asn Ser Leu Val Val Glu
1               5                       10                      15

Ile Pro Pro Phe Arg Asn
            20

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:29:

Gly Ile Leu Lys Leu Arg Asn Ser Asp Ile Glu Leu Arg Lys Gly Glu
1               5                       10                      15

Thr Asp (2) INFORMATION FOR SEQ ID NO:30:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:30:

Leu His Gly Tyr Leu Glu Asn Glu Pro Leu Met Leu Gln Leu Phe Ile
1               5                       10                      15

Gly Thr (2) INFORMATION FOR SEQ ID NO:31:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:31:

Glu Val Gln Pro Lys Ser His His Arg Ala His Tyr Glu Thr Glu Gly
1               5                       10                      15

Ser Arg (2) INFORMATION FOR SEQ ID NO:32:

(i) SEQUENCE CHARACTERISTICS:
        (A) LENGTH: 58 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 17
        (D) OTHER INFORMATION: /label=peptide_spacer
            / note= "Length is at least one a.a. and less than
            1000 a.a., length as well as composition is
            selected independently from the spacer at position -continued ( i x ) FEATURE:
    ( A ) NAME/KEY: Modified-site
    ( B ) LOCATION: 40
    ( D ) OTHER INFORMATION: /label=peptide_spacer
        / note= "Length is at least 1 a.a. and less than
        1000 a.a., length as well as composition is
        selected independently from the peptide spacer at ( x i ) SEQUENCE DESCRIPTION: SEQ ID NO:32:

```
Asn Ala Ile Phe Leu Thr Val Ser Arg Glu His Glu Arg Val Gly Cys
 1               5                  10                     15

Xaa Ala Lys Thr Asp Arg Asp Leu Cys Lys Pro Asn Ser Leu Val Val
             20                  25                  30

Glu Ile Pro Pro Phe Arg Asn Xaa Gly Ile Leu Lys Leu Arg Asn Ser
         35                  40                  45

Asp Ile Glu Leu Arg Lys Gly Glu Thr Asp
 50                  55
```

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ACGCCCAAAG AGGAAAATTT GTTTCATACA        30

( 2 ) INFORMATION FOR SEQ ID NO:34:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
Leu Arg Asn Ser Asp Ile Glu Leu Arg Lys Gly Glu Thr Asp Ile Gly
 1               5                  10                     15

Arg
```

( 2 ) INFORMATION FOR SEQ ID NO:35:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

```
Leu Arg Asn Ala Asp Ile Glu Leu Arg
 1               5
```

( 2 ) INFORMATION FOR SEQ ID NO:36:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:36:

Gly Glu Thr Asp Ile Gly
1               5

(2) INFORMATION FOR SEQ ID NO:37:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: DNA (genomic)

(xi) SEQUENCE DESCRIPTION: SEQ ID NO:37:

Arg Asn Ala Asp Ile Glu
1               5

(2) INFORMATION FOR SEQ ID NO:38:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 3
      (D) OTHER INFORMATION: /mod_base=i (ix) FEATURE:
      (A) NAME/KEY: modified_base
      (B) LOCATION: 9
      (D) OTHER INFORMATION: /mod_base=i (xi) SEQUENCE DESCRIPTION: SEQ ID NO:38:

MGNAAYGCNG AYATHGAR                                          18

(2) INFORMATION FOR SEQ ID NO:39:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 1
      (D) OTHER INFORMATION: /mod_base=i (ix) FEATURE:
      (A) NAME/KEY: modified_base
      (B) LOCATION: 10
      (D) OTHER INFORMATION: /mod_base=i (ix) FEATURE:
      (A) NAME/KEY: modified_base
      (B) LOCATION: 16
      (D) OTHER INFORMATION: /mod_base=i (xi) SEQUENCE DESCRIPTION: SEQ ID NO:39:

NCCDATRTCN GTYTCNCC                                          18

We claim:

1. An isolated polynucleotide comprising at least 25 consecutive nucleotides selected from SEQ. ID NO:1 or its complement, wherein the polynucleotide hybridizes to a polynucleotide having the sequence of SEQ ID NO:1 or its complement.

2. The isolated polynucleotide of claim 1, wherein said polynucleotide comprises at least one polynucleotide sequence selected from the group consisting of: SEQ ID NO:3 through SEQ ID NO. 22.

3. The isolated polynucleotide of claim 2, wherein said polynucleotide comprises one copy of each polynucleotide sequence of SEQ ID NO: 3 through SEQ ID NO:22, and wherein SEQ ID NOS:3 through 22 occur in linear order.

4. The isolated polynucleotide of claim 1, wherein said polynucleotide consists of 2749 consecutive nucleotides which are identical or are complementary to SEQ ID NO: 1.

5. An isolated polynucleotide comprising a nucleotide sequence that encodes human NF-AT$_c$ (SEQ ID NO:2), wherein the human NF-AT$_c$ regulates the transcription of IL-2 in T lymphocytes.

6. A polynucleotide encoding a fusion protein comprising a first amino acid sequence of full-length NF-AT$_c$ (SEO ID NO:2) and a second amino acid sequence.

7. The polynucleotide of claim 6 wherein the second amino acid sequence is an epitope tag.

8. The polynucleotide of claim 6 wherein the fusion protein consists of full-length human NF-AT$_c$ polypeptide fused to a 12 amino acid epitope tag of Hemophilus influenza hemagglutinin.

9. The polynucleotide of claim wherein the nucleotide sequence is the sequence of NF-AT$_c$ from SEQ ID NO: 1.

* * * * *